(12) United States Patent
Earney et al.

(10) Patent No.: US 10,261,018 B2
(45) Date of Patent: Apr. 16, 2019

(54) SOLID INSPECTION APPARATUS AND METHOD OF USE

(71) Applicant: Illumina, Inc., San Diego, CA (US)

(72) Inventors: John Gerhardt Earney, San Diego, CA (US); Joseph Francis Pinto, Solana Beach, CA (US); M. Shane Bowen, Encinitas, CA (US); Michael S. Graige, Cardiff by the Sea, CA (US); Arthur Pitera, Encinitas, CA (US); Bala Murali K. Venkatesan, San Francisco, CA (US); Dajun A. Yuan, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 0 days.

(21) Appl. No.: 15/837,901

(22) Filed: Dec. 11, 2017

(65) Prior Publication Data

US 2018/0195961 A1   Jul. 12, 2018

Related U.S. Application Data

(60) Provisional application No. 62/443,675, filed on Jan. 7, 2017.

(51) Int. Cl.
*G01N 21/64* (2006.01)
*G01J 3/02* (2006.01)
(Continued)

(52) U.S. Cl.
CPC ........ *G01N 21/6456* (2013.01); *G01J 3/0289* (2013.01); *G01J 3/18* (2013.01);
(Continued)

(58) Field of Classification Search
CPC ... G01N 2201/0635; G01N 2021/6417; G01N 21/6458; G01N 21/6486; G01N 21/643;
(Continued)

(56) References Cited

U.S. PATENT DOCUMENTS

| | | | |
|---|---|---|---|
| 2007/0014694 A1* | 1/2007 | Beard | B01L 3/5025 422/400 |
| 2008/0090726 A1* | 4/2008 | Eskra | B41M 5/385 503/207 |
| 2008/0278722 A1* | 11/2008 | Cunningham | G01N 21/6428 356/317 |
| 2010/0187423 A1* | 7/2010 | Nakamura | C01F 17/0018 250/361 R |
| 2011/0031409 A1* | 2/2011 | Cunningham | G01N 21/6428 250/458.1 |

(Continued)

FOREIGN PATENT DOCUMENTS

KR   10-2012-0124227 A   11/2012

OTHER PUBLICATIONS

PCT/US2017/065606, "International Search Report and Written Opinion" dated Mar. 27, 2018, 10 pages.

*Primary Examiner* — Taeho Jo
(74) *Attorney, Agent, or Firm* — Illumina, Inc.

(57) ABSTRACT

An inspection apparatus is provided that comprises an optical target including a solid host material and a fluorescing material embedded in the solid host material. The solid host material has a predetermined phonon energy $HOST_{PE}$. The fluorescing material exhibits a select ground energy level and a target excitation (TE) energy level separated from the ground energy level by a first energy gap corresponding to a fluorescence emission wavelength of interest. The fluorescing material has a next lower lying (NLL) energy level relative to the TE energy level. The NLL energy level is spaced a second energy gap $FM_{EG2}$ below the TE energy level, wherein a ratio of the $FM_{EG2}/HOST_{PE}$ is three or more.

9 Claims, 14 Drawing Sheets

(51) Int. Cl.
*G01N 21/27* (2006.01)
*G01J 3/18* (2006.01)
*G01J 3/44* (2006.01)

(52) U.S. Cl.
CPC .......... *G01J 3/4406* (2013.01); *G01N 21/278* (2013.01); *G01N 21/643* (2013.01); *G01J 2003/1861* (2013.01); *G01N 2201/127* (2013.01)

(58) Field of Classification Search
CPC ......... G01N 21/6456; G01N 2201/127; G01N 35/00732; G01J 1/0266; G01J 3/10; G01J 3/0289
USPC ...................................... 250/252.1
See application file for complete search history.

(56) References Cited

U.S. PATENT DOCUMENTS

| | | |
|---|---|---|
| 2011/0063592 A1 | 3/2011 | Ezura et al. |
| 2011/0259399 A1* | 10/2011 | Shinkai ................ H01L 31/055 136/247 |
| 2012/0280143 A1 | 11/2012 | Kim et al. |
| 2015/0015893 A1 | 1/2015 | Nakahira et al. |
| 2015/0252259 A1* | 9/2015 | Jin ........................ B42D 25/29 250/459.1 |
| 2016/0160276 A1* | 6/2016 | Earney .............. B01L 3/502723 348/135 |
| 2016/0377561 A1 | 12/2016 | Ramachandran et al. |
| 2017/0276614 A1* | 9/2017 | Bovero .............. G01N 21/8851 |

* cited by examiner

SOLID INSPECTION APPARATUS AND METHOD OF USE

CROSS-REFERENCE TO RELATED APPLICATIONS

This application claims the benefit of U.S. provisional application Ser. No. 62/443,675, filed Jan. 7, 2017, the contents of which is incorporated by reference herein in its entirety.

BACKGROUND

Optical targets are frequently used in calibration, alignment and measurement in optical systems. The optical targets are utilized, among other things, when determining accuracy and performance of the optical system. By way of example, the optical target affords a basis, with respect to which the system may quantify optical resolution, depth of focus, optical and mechanical drift, distortion, lens-based aberration, chromatism and the like.

However, some pre-existing optical targets have experienced certain limitations. For example, some pre-existing optical targets include channels that convey liquids that have a fluorescing dye provided therein, where the dye emits fluorescence in a desired emission spectra. Some pre-existing optical targets include inlet and outlet ports to allow the liquid dye within the channels to be replaced, which allows different dye materials to be utilized in a common optical target at different points in time. However, the use of channels and inlet and outlet ports increases the fluidic complexity of the optical target. In addition, particular operations may have to be followed in order to avoid the introduction of air bubbles into the channel of the optical target when liquid dye materials are changed or passed through the channels.

There is a need for tools that facilitate accurate calibration of alignment and validation of optical detection systems.

Definitions

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

As used herein, the following terms have the meanings indicated.

The term "solid host material" refers to materials that have an atomic or molecular structure arranged in a lattice or other matrix such that the solid host material exhibits a predetermined phonon energy $HOST_{PE}$. Solid host materials may comprise any crystalline, semi-crystalline or amorphous material capable of being doped or otherwise embedded with a fluorescing material as described herein. For example, ceramic represents one example of a crystalline material. Glass and some polymers may represent non-crystalline or semi-crystalline materials that may be doped/embedded with fluorescing materials of interest. The choice of the solid host material is determined (at least in part) by the application in which the solid host material is to be used. For example, in many applications, the solid host material choice is based on its mechanical properties (e.g., hardness), chemical stability/inertness, thermal properties and/or optical properties. Microscopic properties such as lattice arrangement, chemical structure and phonon spectrum may also be relevant when choosing the solid host material. For example, lattice and chemical structure play a role in terms of specific dopant type and concentration, while the optical phonon spectrum affects the quantum efficiency of a specific transition via non-radiative decay.

The term "fluorescing material" refers to one or more chemical elements, combinations of chemical elements or other materials that are added to the solid host material and that fluoresce, alone or in cooperation with the solid host material, when excited. For example, the solid host material may be infused or doped with one or more chemical elements, such as transition metal ions, rare-earth lanthanide ions, and/or actinide ions. The fluorescing material may be referred to as a dopant, such as when transition metal ions, rare-earth lanthanide ions, and/or actinide ion are added to a solid host material. The fluorescing material may comprise a single element or may comprise a combination of elements (e.g., co-dopants). It is recognized that, while the term "fluorescing material" refers to the one or more elements that are added to the solid host material, in at least some examples, the element(s) added to the solid host material may not fluoresce independent of the solid host material. Instead, the one or more elements form a fluorescing material when cooperating with the solid host material. Optionally, in alternative examples, the element(s) added to the solid host material may fluoresce independent of the solid host material. Optionally, the fluorescent material may represent a fluorescent dye embedded within epoxy. As another example, a fluorescent film may be coated on top of an optical target in addition to or in place of doping fluorescent material within a solid host material.

The term "quantum dots" (QD) refers to very small semiconductor particles (e.g., several nanometers in size) that have optical and electronic properties that differ from the properties of larger particles. The quantum dots are designed to emit light of specific frequencies of interest in response to electricity or light applied thereto. The emission frequencies may be tuned by changing the dot size, shape and/or material. In some examples, nanoscale semiconductor materials tightly confine either electrons or electron holes. By way of example, quantum dots may also be referred to as artificial atoms, a term that emphasizes that a quantum dot is a single object with bound, discrete electronic states, as is the case with naturally occurring atoms or molecules. Quantum dots have optoelectronic properties that change as a function of both size and shape. Larger QDs (radius of 5-6 nm, for example) emit longer wavelengths resulting in emission colors such as orange or red. Smaller QDs (radius of 2-3 nm, for example) emit shorter wavelengths resulting in emission colors like blue and green, although the specific colors and sizes vary depending on the exact composition of the QD.

The term "solid body" includes any non-liquid, non-gaseous substrate that is utilized to enclose fluorescing material. One example of a solid body is a solid host material that has one or more fluorescing materials doped or otherwise embedded within the solid host material. Another example of a solid body includes a non-liquid, non-gaseous substrate to enclose quantum dots.

As used herein, relative or spatial terms such as "top," "bottom," "front," "rear," "first," "second," "upper," and "lower" are used as terms of direction with respect to a reference object, point or axis. In accordance with examples disclosed herein, the relative or spatial terms are used relative to the objective in the instrument when positioned adjacent to the inspection apparatus. For example, structures, portions, and/or surfaces of the inspection apparatus that are proximate/closest to the objective may be referred to as "top", "upper", etc. Similarly, structures, portions, and/or surfaces of the inspection apparatus that are remote/further from the objective may be referred to as "bottom", "lower", etc.

SUMMARY

In accordance with examples disclosed herein, an inspection apparatus is provided that comprises an optical target including a solid host material and a fluorescing material embedded in the solid host material. The solid host material has a predetermined phonon energy $HOST_{PE}$. The fluorescing material exhibits a select ground energy level and a target excitation (TE) energy level separated from the ground energy level by a first energy gap corresponding to a fluorescence emission wavelength of interest (FEWI). The fluorescing material has a next lower lying (NLL) energy level relative to the TE energy level. The NLL energy level is spaced a second energy gap $FM_{EG2}$ below the TE energy level, wherein a ratio of the $FM_{EG2}/HOST_{PE}$ is three or more.

Optionally, the ratio of the $FM_{EG2}/HOST_{PE}$ equals or is between four and ten. Optionally, the solid host material includes at least one of glass, amorphous polymers, crystalline materials, semi-crystalline polymers, metallic glass, or ceramic. Optionally, the fluorescing material represents an ion of at least one of a rare-earth element or a transition metal element. Optionally, the solid host material has a maximum phonon energy less than or equal to 580 $cm^{-1}$. Optionally, the fluorescence emission wavelength of interest has a center wavelength at or below 1000 nm.

Optionally, the apparatus may further comprise a body having a pocket to receive the optical target, wherein the body includes an inset region located at a top surface and surrounding the pocket; and a transparent layer mounted in the inset region and positioned above the optical target. Optionally, the body includes a channel at least partially surrounding the pocket, the channel to receive an adhesive to bond to a grating layer. The channel includes a series of pressure relief pockets distributed about the channel. The pressure relief pockets are to relieve stress induced onto the grating layer by the adhesive during a curing process. Optionally, the body may further comprise microstructures formed on a surface of at least one of the transparent layer or the optical target to form a grating layer. Optionally, the apparatus may further comprise an optical target retention body having a pocket to receive the optical target. The body may be formed of aluminum that includes a surface having a reflectivity of no more than about 20%. The body may include an inset region located at the top surface and surrounding the pocket. The apparatus may further comprise a transparent grating layer mounted in the inset region and that may be positioned above the optical target and spaced apart from the optical target by a fringe gap. As mentioned above, the body may include a pocket to receive the optical target. The body may include a diffusion well located below the pocket. The diffusion well may receive excitation light passing through the optical target. The diffusion well may include a well bottom having a surface finish that exhibits a reflectively of no more than about 20.0%. The apparatus may further comprise an anti-reflective coating formed on a surface of at least one of the transparent layer or the optical target.

Optionally, in accordance with an alternative example, the inspection apparatus may include an optical target and a transparent layer directly bonded onto one another without any additional supporting body structure. Microstructures may be provided at the interface between the optical target and transparent layer. The microstructures may represent one or more chrome patterns formed on a top surface of the optical target and/or on a bottom surface of the transparent layer. Optionally, in accordance with an alternative example, the inspection apparatus may be utilized as an inspection apparatus located directly on a flow cell, instead of being mounted into an instrument. Optionally, the transparent layer may be omitted entirely. Optionally, the optical target may be utilized as a stand-alone inspection apparatus without a transparent layer or any other supporting structures, such as the body.

It is to be understood that any features of the inspection apparatus may be combined together in any desirable manner and/or configuration.

In accordance with examples herein, an optical detection device is provided. The optical detection device includes an optical target, which includes a solid body that encloses a fluorescing material. An objective directs excitation light toward the optical target and receives fluorescence emission from the optical target. A driver moves the objective to a region of interest proximate to the optical target. A memory to store program instructions is also part of the optical detection device. A processor executes the program instructions for detecting fluorescence emission from the optical target in connection with at least one of optical alignment or calibration of an instrument.

Optionally, the objective may direct excitation light onto the optical target. The processor may derive reference information from the fluorescence emission. The processor may utilize the reference information in connection with the at least one of optical alignment or calibration of the instrument. The optical target may be permanently mounted at a calibration location proximate to the objective. The calibration location may be separate from flow cell channels within the instrument. Optionally, the optical target includes a solid host material and a fluorescing material embedded in the solid host material, the solid host material having a predetermined phonon energy $HOST_{PE}$. The fluorescing material exhibits a select ground energy level, a target excitation (TE) energy level and a next lower lying (NLL) energy level spaced an energy gap $FM_{EG2}$ below the TE energy level, wherein a ratio of the $FM_{EG2}/HOST_{PE}$ is three or more.

The solid body may represent a substrate comprising a solid host material with the fluorescing material embedded in the solid host material. The solid body may represent at least one of an epoxy or polymer that encloses quantum dots that emit fluorescence in one or more predetermined emission bands of interest when irradiated by the excitation light.

In an example, the optical detection device further comprises an anti-reflective coating formed on the optical target.

It is to be understood that any features of the optical detection device may be combined together in any desirable manner. Moreover, it is to be understood that any combination of features of the optical detection device and/or of the inspection apparatus may be used together, and/or that any features from either or both of these aspects may be combined with any of the examples disclosed herein.

In accordance with examples disclosed herein, a method is provided. The method aligns an objective of an instrument with an optical target that includes a solid body that encloses a fluorescing material. The method directs excitation light onto the optical target, detects fluorescence emission from the optical target as reference information and utilizes the reference information in connection with at least one of optical alignment or calibration of the instrument.

Optionally, the method may further comprise focusing the excitation light to a focal point that may be below an upper surface of the optical target.

The aligning operation may comprise aligning the objective with a grating region that includes a microstructure located above the optical target and focusing the excitation light to a first focal point at the microstructure, and aligning the objective with a non-grating region that is void of the microstructure and focusing the excitation light to a second focal point that is below an upper surface of the optical target. Optionally, the fluorescing material may comprise a chemical element that comprises an ion of at least one of erbium, holmium or praseodymium and the solid host material comprises at least one of Silicate, Germanate, $InF_3$, or ZBLAN (i.e., heavy metal fluoride glasses, such as $ZrF_4$—$BaF_2$—$LaF_3$—$AlF_3$—NaF).

It is to be understood that any features of the method may be combined together in any desirable manner. Moreover, it is to be understood that any combination of features from the method and/or the optical detection device and/or the inspection apparatus may be used together, and/or that any features from any or all of these aspects may be combined with any of the features of the examples disclosed herein.

BRIEF DESCRIPTIONS OF THE DRAWINGS

DETAILED DESCRIPTION

Examples disclosed herein describe optical targets that utilize solid bodies with fluorescing material therein. The optical target may be used to calibrate the optics of fluorescence-based optical systems with a predetermined level of precision and accuracy, such as in a nanometer scale, or a micrometer scale, etc., depending upon the optical property being measured. One or more of the examples disclosed herein afford significant benefits. For example, a solid body target system is relatively easy to fabricate as compared to conventional liquid die based targets and fluidic counterpart targets. A solid body target system exhibits a relatively long shelf life, as the parts do not leak or photo-degrade over time. Also, the solid body target system does not require custom in-house processes and hence can be readily outsourced to suppliers. Also, the solid body target system enables fluorescence emission that is constant over time without photo-degradation at a given optical power, which provides the potential that a solid body target system can be used for power metering and power calibration of instrument illumination sources while in the field. Integrating the foregoing functionalities permanently into a sequencing system enables remote system monitoring to improve instrument up time.

Figure 1A:
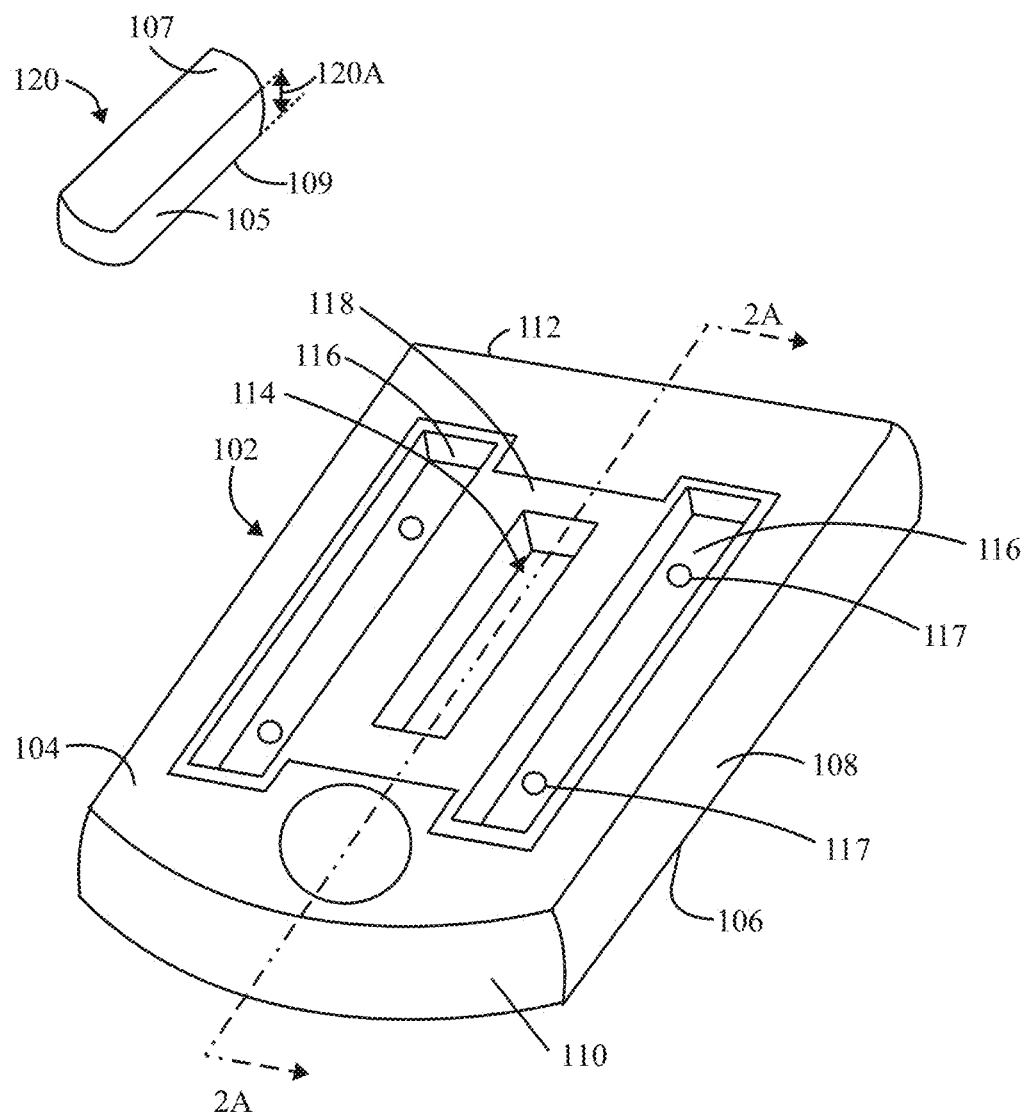
FIG. 1A illustrates a perspective view of an inspection apparatus formed in accordance with an example herein, where an optical target is shown separate from a body that is to receive the optical target.

FIG. 1A illustrates a perspective view of an inspection apparatus 100 formed in accordance with an example disclosed herein. The inspection apparatus 100 includes a body 102 having top and bottom surfaces 104, 106 that extend generally planar to one another. The body 102 may include rounded corners that transition between lateral sides 108 and front and back ends 110, 112. In the present example, the body 102 is rectangular in shape, although alternative shapes may be utilized. The inspection apparatus 100 is shaped and dimensioned to be mounted within an instrument that performs optical measurements and analysis. By way of example, the instrument may be a fluidics instrument, although the examples disclosed herein may be utilized with non-fluidic optical instruments. As examples, the inspection apparatus 100 described herein may be utilized in connection with micro-fluidics, semiconductors, biotechnology and consumer industry instruments. For example, the inspection apparatus 100 may be utilized for alignment of a semiconductor tool, such as mask aligners and steppers, for calibration of a machine vision system, for optical stages in applications such as optical coherence tomography and fluorescence-based biological imaging. As another example, the inspection apparatus 100 may be utilized in connection with calibration of standard consumer optical tools such as fluorescence microscopes.

Examples herein may be utilized in connection with next generation sequencing systems that utilize various fluorescence methods. For example, the inspection apparatus 100 may be utilized in connection with the MINISEQ® instrument, HISEQ® instrument, NEXTSEQ® instrument and MISEQ® instrument offered by Illumina Inc. (San Diego, Calif.) and/or in connection with instruments offered by other companies. In accordance with at least some examples, the inspection apparatus 100 enables the optical calibration of an instrument without a need for fluorescent reference particles or fluorescent dies (as conventionally used). Conventional fluorescent reference particles and dies provide calibration for a few of the more frequently used fluorophores (e.g., Fluorescein and Phycoerythin). However, conventional fluorescent reference particles and dyes suffer from thermal and photo-stability, leakage and/or mechanical failure.

In accordance with the examples provided herein, the inspection apparatus 100 may be utilized as a built-in remote diagnostic optical target. The inspection apparatus 100 may be permanently mounted within an instrument and positioned to enable a detector within the instrument to perform optical measurements without having to manually load any additional tool. The inspection apparatus 100 may be used, by the instrument, to provide remote diagnostic information in connection with various activities. For example, the instrument may utilize the inspection apparatus 100 to perform data trending such as trends in a point spread function of an instrument, laser alignment, optical calibration, and optical transmission efficiency over the life of the instrument. Data can be collected automatically with no user intervention and uploaded to the cloud in order to perform remote debugging, perform predictive diagnostics, and trend across multiple instruments. The inspection apparatus 100 may be utilized to evaluate various aspects of the instrument's optical system, as well as aspects of the XYZ stages. For example, if the laser alignments are found to be off, software can automatically actuate the pointing mirrors to bring the laser into alignment.

In accordance with some examples, an inspection apparatus 100 may be assembled and shipped with each instrument, where the instrument includes a current software release of an inspection application that controls the instrument to carry out various tests with the inspection apparatus 100. When the inspection apparatus 100 is dimensioned to be loaded and unloaded, the inspection apparatus 100 may be configured as a full-sized inspection apparatus that may be used for measuring optical metrics. The full-sized inspection apparatus will mate with a flow cell holder and be utilized to evaluate flow cell holder alignment. The full-size inspection apparatus will extend the full length of a sequencing flow cell to enable a simulation of a sequencing run. Optionally, the inspection apparatus 100 may be reduced in size and mounted within the instrument at a staging location, adjacent to the flow cell lanes. When the inspection apparatus 100 is permanently mounted within the instrument (at a reduced footprint), the instrument may perform inspection operations without a need to load and unload the inspection apparatus 100. The reduced footprint inspection apparatus may be utilized to perform optical metrics.

An optical target 120 includes top and bottom target surfaces 107, 109 that are generally planar and oriented parallel to one another. A sidewall 105 extends about the optical target 120. In the present example, the optical target 120 generally has a rectangular cubical shape, although it is recognized that alternative shapes may be utilized based upon a particular application. As explained herein, the optical target 120 represents a solid body structure that includes a solid host material and a fluorescing material embedded within the solid host material. The solid host material may be entirely or at least partially transparent. For example, a degree of transparency in the solid host material may be based, in part, on a desired intensity of fluorescing emissions that are emitted from the optical target 120. By way of example, the solid host material of the solid body structure or substrate may represent a glass substrate or another solid host material having desired mechanical and optical properties as described herein.

As one example, the host solid material may be indium-fluoride glass. For example, the solid host material may include at least one of glass, amorphous polymers, crystalline materials, semi-crystalline polymers, metallic glass, ceramic and the like. Table 1 below illustrates examples of solid host materials that may be utilized within the solid body structure or substrate. As illustrated in Table 1, the solid host material may represent heavy metal fluoride glasses (e.g., ZBLAN). ZBLAN glass may utilize various combinations with fluoride, such as $ZrF_4$, $BaF_2$, $LaF_3$, $AlF_3$, and $NaF$. Optionally, the solid host material may be $CaF_2$. The solid host materials exhibit low maximum phonon energy levels. In accordance with some examples, the solid host material may exhibit a maximum phonon energy of less than or equal to a predetermined wave number. As a further example, the solid host material may exhibit a maximum phonon energy of or between about 370 $cm^{-1}$ and about 525 $cm^{-1}$. The solid host material may be formed of other materials that include low maximum phonon energy and exhibit available energy bands at locations of interest to obtain fluorescing within emission bands that correspond to optical channels of interest.

TABLE 1

| Glass Former | Maximum phonon energy ($cm^{-1}$) |
|---|---|
| $ZrF_4$ | 580 |
| $HfF_4$ | 580 |
| $GaF_3$ | 525 |
| $InF_3$ | 510 |
| $CdF_2/CdCl_2$ | 370 |

The fluorescing material may be a rare-earth element such as rare earth ions: $Tm^{3+}$ (455 nm), $Ho^{3+}$ (550 nm), $Tb^{3+}$ (540 nm), $Eu^{3+}$ (611 nm), $Sm^{3+}$ (550 nm), $Pr^{3+}$ (488, 590 nm), $Dy^{3+}$ (480 nm & 575 nm), or $Er^{3+}$ (550 nm & 660 nm); an element from the Actinide series: U; transition metal ions: $Ti^{3+}$, $Cr^{2+/3+}$, etc. The fluorescing material may be distributed in an even and homogeneous fixed manner throughout the solid host material, such as to form Er—$InF_3$ glass. The fluorescing material emits in one or more emission channels of interest. For example, the fluorescing material may emit at a wavelength shorter than 1000 nm.

The fluorescence material may be provided in various concentrations within the solid host material, where the concentration of the fluorescing material is managed based, in part, on a desired intensity of fluorescence emission to be obtained in response to an expected excitation light intensity. In the above example, when the host substrate is indium-fluoride (InF$_3$) glass doped with trivalent erbium ions, the trivalent erbium ions may be provided at a dopant concentration at or between about 0.1% and about 10.0% and, for example, at or between about 0.5% and about 6% by atomic fraction. As another example, the dopant concentration of trivalent erbium ions may range from about 1.0% to 3.0%+/−0.01% by atomic fraction. The fluorescing material exhibits a select emission intensity that may be tuned by adjusting the composition. For example, the emission intensity and/or color may be varied by adjusting the concentration of the fluorescing material, by adding a secondary dopant (e.g., co-dopant), and/or by adjusting the composition of the solid host material. For example, a first dopant may represent a primary dopant or activator ion, while a secondary dopant may be added to increase or decrease the emission intensity of the primary dopant. The secondary dopant represents a sensitizer ion. Combining more than one dopant may enhance fluorescent intensity. By co-doping with an additional sensitizer ion, the emission intensity can be increased by energy transfer between the sensitizer ion and the activator ion (e.g., Er). For example, $Yb^{3+}$ or $Tm^{3+}$ may be used as a sensitizer ion when $Er^{3+}$ is used as the activator ion. As other examples, Yb, Ho and $YF^3$ may be used as sensitizer ions.

Optionally, combining more than one dopant may be used to decrease fluorescent intensity of one or more emission bands. By co-doping with an additional sensitizer ion, the emission intensity can be decreased by energy transfer between the sensitizer ion and the activator (e.g., Er). For example, Tb/Eu may be co-doped in $Yb_2O_3$, where the energy transfer from Tb to Eu results in emission changes from red to green. As another example, Tm may be co-doped with Tb or Ho to promote continuous wave (cw) lasing at 1.5 microns (μm). Examples of combinations for co-doping are described in: "Properties of the 1.5 and 2.3 μm laser emissions of various Tm doped fluoride crystals codoped with Tb or Yb ions" published in OSA TOPS Vol. 26 Advanced Solid-State Lasers; "Ultraviolet and visible emissions of $Er^{3+}$ in $KY(WO_4)_2$ single crystals co-doped with $Yb^{3+}$ ions" published in Journal of Luminescence 115 (2005) 131-137; "Color-tunable properties of $Eu^{3+}$- and $Dy^{3+}$-codoped $Y_2O_3$ phosphor particles published in Nanoscale Res Lett. 2012; 7(1):556; and the book "Current Trends in Optical Amplifiers and Their Applications" edited by Tien-Pei Lee, the complete subject matter of which are incorporated by reference in their entirety.

The solid host material and the dopant may be chosen such that the combination exhibits a desired energy level ratio. For example, the combination may exhibit an energy level ratio of $HOST_{PE}/FM_{ET}$, where the $HOST_{PE}$ represents the maximum phonon energy of the solid host material and $FM_{ET}$ represents the energy transition between a target emission energy level and a nearest neighbor energy level of the fluorescing material.

In accordance with examples disclosed herein, the solid host material and the fluorescing material exhibit an energy level ratio of $FM_{EG2}/HOST_{PE}>=(\geq)4$, where the $HOST_{PE}$ represents the phonon energy of the solid host material and $FM_{EG2}$ represents the energy transition between a target excitation energy level and a next lower lying (NLL) energy level of the fluorescing material. By way of example, Table 2 is provided below to show a relationship for an example fluorescing material energy gap $FM_{EG2}$ with various solid host materials. For example, the fluorescing material may represent a trivalent erbium ion ($Er^{3+}$) element where the TE energy level is the $^4F_{9/2}$ energy level and the NLL energy level is the $^4I_{9/2}$ energy level. The energy gap between the $^4F_{9/2}$ and $^4I_{9/2}$ energy levels is a wave number of 2900 cm$^{-1}$. In Table 2, example solid host materials include silicate, germanate and ZBLAN which have maximum phonon energies of 1100 cm$^{-1}$, 900 cm$^{-1}$, and 500 cm$^{-1}$, respectively. The energy level ratio for trivalent erbium ion ($Er^{3+}$) and the solid host materials silicate, germanate and ZBLAN ($FM_{EG2}/HOST_{PE}$) are 3, 4 and 6, respectively, while the quantum efficiencies are about 0.22%, 14% and 90%, respectively. The "quantum efficiency" (Q.E.) is a ratio of the number of emitted fluorescing photons to a number of incident excitation light photons. As evident in Table 2, ZBLAN exhibits a high degree of quantum efficiency as compared to silicate and germanate for the particular fluorescing material $Er^{3+}$. Optionally, silicate and germanate may be afforded a higher quantum efficient than illustrated in Table 2 when a different fluorescing material is utilized as a dopant. For InF$_3$ glass doped with $Er^{3+}$, the energy level ratio is 6, corresponding to a quantum efficiency of about 90%. It is recognized that other fluorescing materials will exhibit different quantum efficiencies with the listed solid host materials.

TABLE 2

| Host material | Maximum phonon energy | Energy Level Ratio ($FM_{EG2}/HOST_{PE}$) for $Er^{3+}$ | Quantum Efficiency |
|---|---|---|---|
| Silicate | 1100 cm$^{-1}$ | 3 | 0.22% |
| Germanate | 900 cm$^{-1}$ | 4 | 14% |
| ZBLAN | 580 cm$^{-1}$ | 5 | 85% |
| InF3 | 500 cm$^{-1}$ | 6 | 90% |

With continued reference to FIG. 1A, the body 102 may comprise aluminum or another material having similar mechanical and optical properties. The body 102 may be formed through a milling process or another manufacturing process that affords desired tolerances for the various ledges, walls, wells, etc. discussed herein. The body 102 includes an inset region 118 provided across the top surface 104. A central pocket 114 and channels 116 are provided within an interior area of the inset region 118. The central pocket 114 is configured to receive the optical target 120. The optical target 120 may be secured within the pocket 114 in various manners, such as with an adhesive. Optionally, the pocket 114 may be formed with peripheral features that securely engage with peripheral walls of the optical target 120 (e.g., in a press fit manner). The inset region 118 is configured to receive a glass layer (not shown in FIG. 1A) or other transparent material (i.e., transparent layer) that covers the optical target 120 into the pocket 114. The channels 116 receive an adhesive that bonds to the glass layer and the body 102, thereby covering and hermetically sealing the optical target 120 from the external environment. In accordance with at least some examples, the layer of glass may have microstructures formed thereon, thereby defining a grating layer (e.g., 122 in FIG. 2A). Optionally, the glass layer may be omitted entirely and the optical target 120 may be exposed from the top surface 104 of the body 102.

In the example of FIG. 1A, the central pocket 114 is elongated and positioned to extend in a longitudinal direction along a length of the body 102. The channels 116 are formed along opposite sides of the pocket 114. The channels 116 include one or more inlet/outlet ports 117 in the bottom thereof that extend from the bottom of the channels 116 to the bottom surface 106 of the body 102. The inlet/outlet ports 117 may be used to inject the adhesive into the channels 116 after the top glass has been inserted into the inset region 118.

Optionally, the optical target 120 may be utilized as a stand-alone inspection apparatus with no microstructures or other patterns formed thereon or provided proximate thereto. For example, the optical target 120 may simply be mounted directly on a flow cell and/or within an instrument without any other supporting structures.

Figure 1B:
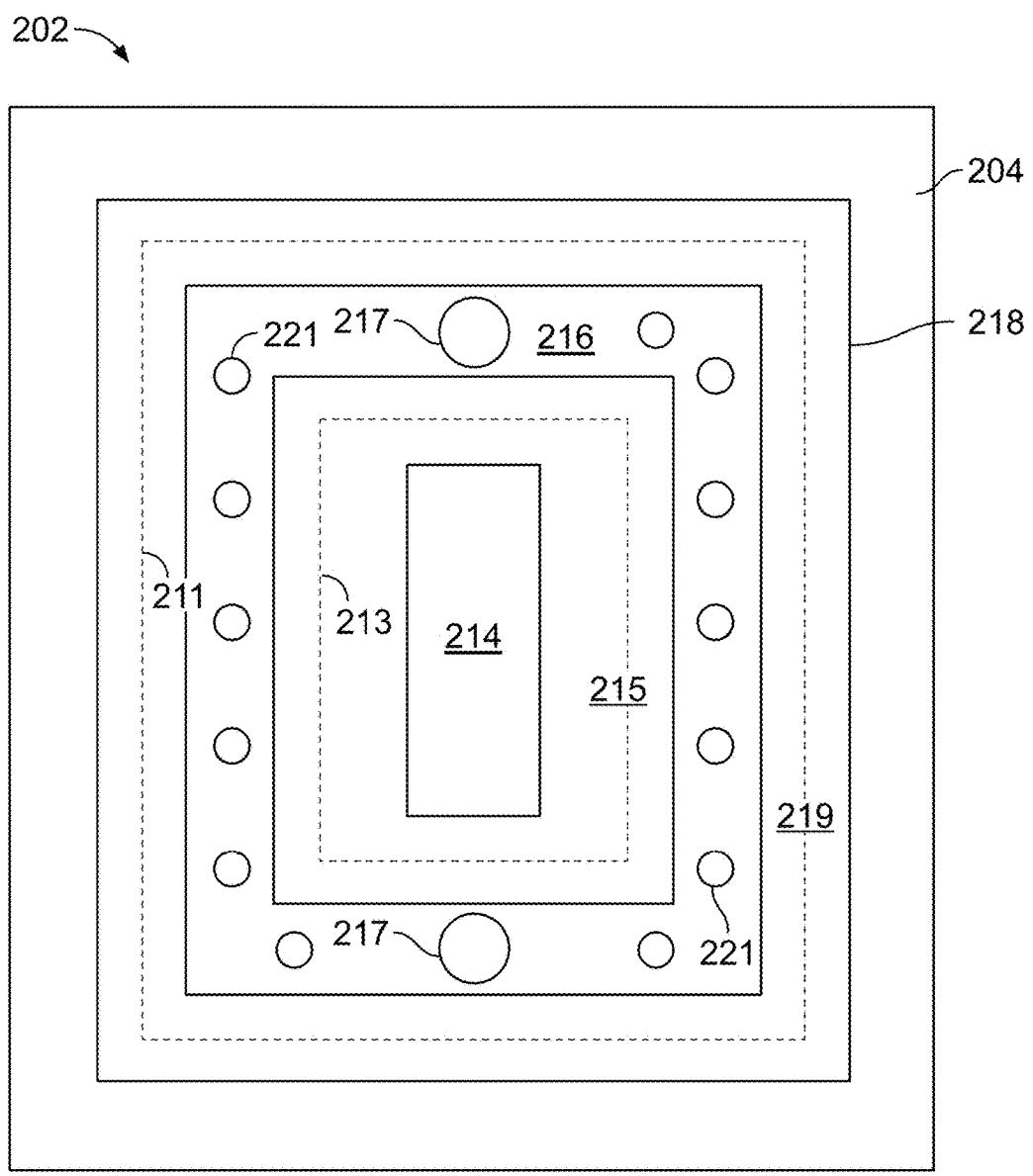
FIG. 1B illustrates a top plan view of a body formed in accordance with an alternative example.

FIG. 1B illustrates a top plan view of a body 202 formed in accordance with an alternative example. The body 202 includes a top surface 204 that includes an inset region 218 formed therein. The inset region 218 is shallow and extends a depth downward into the body 202, where the depth generally corresponds to the thickness of a glass layer (e.g., grating layer) to be received in the insert region 218. In the example of FIG. 1B, the inset region 218 is generally square or rectangular, although alternative shapes may be utilized. Further, in the example of FIG. 1B, the inset region 218 has a generally even/common depth corresponding to the thickness of the glass layer. However, the inset region 218 may have varied depths in different regions thereof, such as when it is desirable to utilize a glass layer with portions having different thicknesses and/or separate pieces to form the glass layer.

The body 202 also includes a pocket 214 generally centered within the inset region 218. The pocket 214 is shaped and dimensioned to receive the optical target 120. The pocket 214 extends a predetermined depth below a depth of the inset region 218. A channel 216 is provided within the inset region 218 and positioned to substantially surround of the pocket 214. The channel 216 generally corresponds to the channel 116 in FIG. 1A, except that the channel 216 is continuous to surround the pocket 214. The channel 216 includes inlet/outlet ports 217 that represent holes extending through the body 202 to the bottom surface thereof. The inlet/outlet ports 217 may be utilized to access the interior of the glass layer once inserted and to insert an adhesive into the channel 216.

In an example, the channel 216 also includes a series of pressure relief pockets 221 distributed about the channel 216. As explained below in more detail, the pressure relief pockets 221 relieve stress induced on the glass layer by the adhesive silicone added to the channel 216. More specifically, when silicone is introduced into the channel 216 through the inlet/outlet ports 217, the silicone at least partially bridges over the pockets 221, thereby trapping small amounts of air in each of the pockets 221. As the silicone cures, the silicone contracts, thereby introducing a drawing/shrinking force on to the grating layer and surrounding walls of the channel 216. The air trapped in the pockets 221 form a first region of relief for the silicone, thereby reducing the drawing force applied by the silicone onto the grating layer.

The pocket 214 and channel 216 are separated by an interior ledge 215 that, in the example of FIG. 1B, is also rectangular. It is recognized that any of the square or rectangular geometries illustrated in FIG. 1B may be modified to resemble numerous alternative shapes. The channel 216 is surrounded on an outer perimeter thereof by an exterior ledge 219. The interior and exterior ledges 215 and 219 form a shelf that receives the glass layer.

When assembled, the optical target 120 is inserted into the pocket 214 and may be retained therein with an adhesive, by frictional interference between the walls of the pocket 214 and the sides of the optical target 120, and the like. Once the optical target 120 is inserted into the pocket 214, the glass layer is inserted into the inset region 218 until resting on the interior and exterior ledges 215, 219. In accordance with some examples disclosed herein, the inset region 218 receives a transparent layer (e.g., formed of glass and thus also referred to as the glass layer) that functions as a grating layer (e.g., see 122 in FIG. 2A). The grating layer is sealed into the inset region 218 to prevent contaminants from getting into the pocket 214 after assembly is complete. For example, end users may wipe the inspection apparatus periodically with cleaners (e.g., alcohol) to clean it. Examples herein utilize an alcohol resistant adhesive that is injected into the channel 216 to attach the grating layer to the body 202, where the adhesive will hold up well to alcohol exposure. For example, the adhesive may be silicone which is highly stable in alcohol, whereas UV cure adhesives tend to break down in alcohol. The silicone is injected until the channels 116 are filled. However, silicone may exhibit "outgassing" when curing.

Examples disclosed herein isolate the pocket 214 and optical target 120 from the byproducts of the outgassing process. To do so, once the grating layer is inserted into the inset region 218 and resting on the interior and exterior ledges 215, 219, an outgassing barrier 213 is formed about the interface between the grating layer and the interior ledge 215. An outgassing barrier 211 is also formed about the interface between the grating layer and the exterior ledge 219. The outgassing barriers 213, 215 may be formed by injecting a tool through one or more of the inlet/outlet ports 217 and depositing a predetermined volume of a barrier adhesive along the edge of the interface between the grating layer and the interior ledge 215, and along the edge of the interface between the grating layer and the exterior ledge 219. For example, the barrier adhesive may be a low-viscosity (e.g., 300 cp) UV cure adhesive. After waiting a predetermined period of time, the barrier adhesive wicks across the interior and exterior ledges 215 and 219 to form thin bonding layers between the interior ledge 215, exterior ledge 219 and the grating layer (denoted by the dashed lines 211, 213 as outgassing barriers). The grating layer will be in a stress-free state and pulled down to the interior and exterior ledges 215, 219. UV curing in this state maintains the grating layer flat and properly positioned without using any clamping fixtures which could bend the grating layer. Additionally the outgassing barrier 213 at the interior ledge 215 prevents any silicone outgassing from getting into the pocket 214.

Figure 1C:
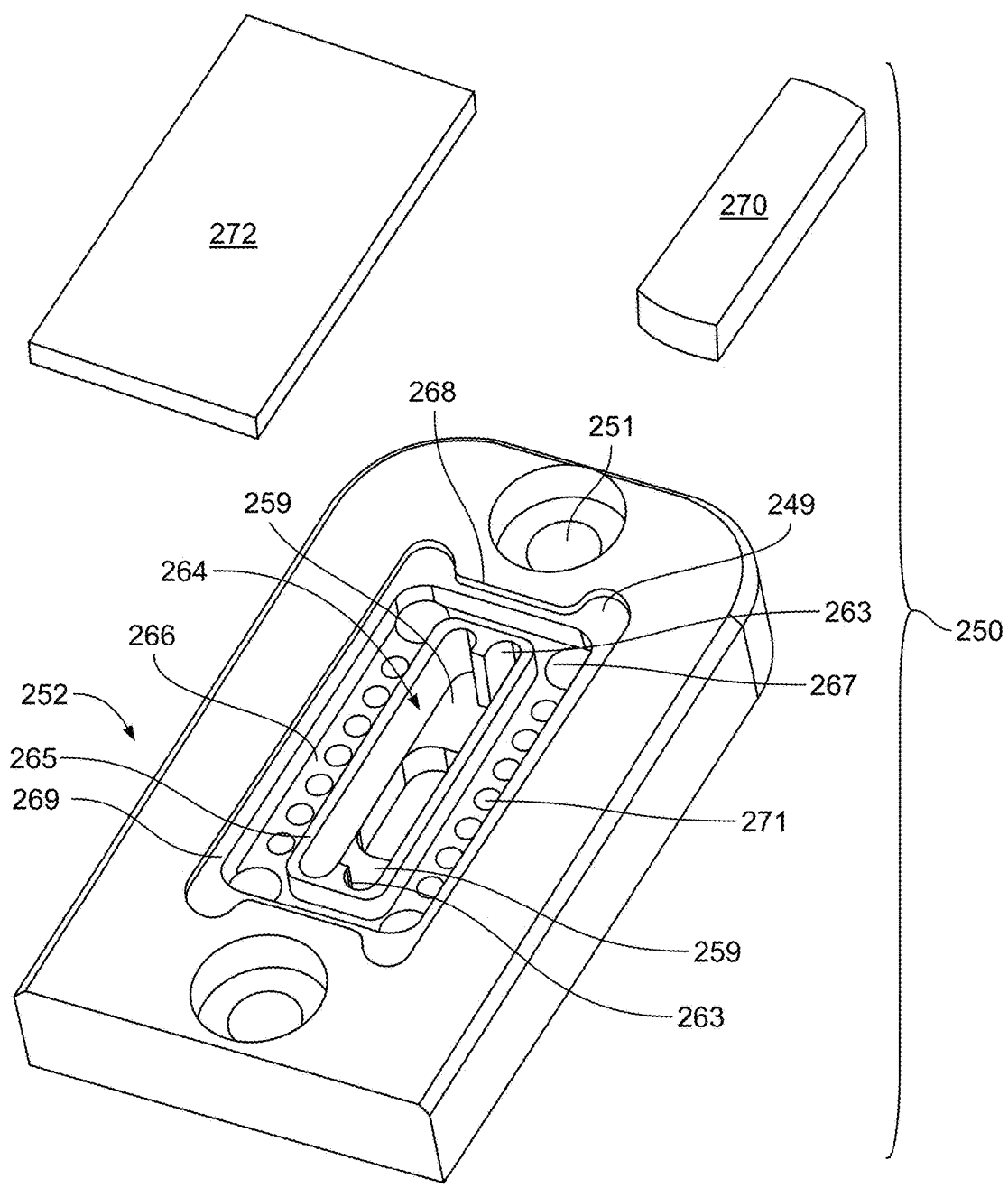
FIG. 1C illustrates a perspective view of an inspection apparatus formed in accordance with an alternative example, where an optical target and a grating layer are shown separate from a body that is to receive the optical target and the grating layer.

FIG. 1C illustrates a perspective view of an inspection apparatus 250 formed in accordance with an alternative example. The inspection apparatus 250 includes a body 252, an optical target 270, and a grating layer 272. The body 252 includes a pocket 264 generally centered within an inset region 268. The pocket 264 is shaped and dimensioned to receive the optical target 270. A channel 266 is provided within the inset region 268 and positioned to substantially surround of the pocket 264. The channel 266 includes inlet/outlet ports 267. The inset region 268 includes an interior ledge 265 and an exterior ledge 269 that are arranged in a coplanar manner and positioned to receive a lower surface of the grating layer 272. The body 252 is formed in a manner to maintain a desired amount of flatness in grating layer 272. Maintaining a desired amount of flatness in the grating layer 272 is beneficial as some optical calibrations utilize a flat region of the chrome pattern. When silicone cures, it may shrink which may pull the grating layer 272 down into the channel 266, unless otherwise corrected. If the grating layer 272 is pulled into the channels 266, a central portion of the grating layer 272 may bow upward in the region over the optical target 270. Also, clamping the top glass (grating layer 272) in position during adhesive curing may bend the grating layer 272 in a manner that becomes permanent when the adhesive cures in this state.

In accordance with examples herein, the top surface of the grating layer 272 is maintained with a desired amount of flatness/planar geometry. To do so, the channel 266 is provided with a series of pressure relief pockets 271 distributed about the channel 266. The pressure relief pockets 271 relieve stress induced on to the grating layer 272 by the adhesive silicone added to the channel 266 during the curing process. Some of the examples disclosed herein prevent the silicone, when curing, from pulling the grating layer 272 down into the channel 266. The UV cure adhesive (barriers 211, 213 in FIG. 1B) holds the grating layer 272 down on both sides of the channel 266, thereby avoiding bending (or at least substantially reducing bending) of the grating layer 272. The potential for bending of the grating layer 272 is further reduced by leaving part of the channel 266 unconstrained so that the silicone can shrink without pulling on the grating layer 272. This may be achieved by making periodic pockets 271 (holes) in the bottom of the channel 266. When silicone is flowed through the channel 266, air is trapped inside the pockets 271. When the silicone cures, air bubbles are free to expand up into the channel 266 as the silicone shrinks. It is much easier to pull the air bubble up into the channel 266 than it is to pull the grating layer 272 down into the channel 266, so the grating layer 272 does not deform during curing.

Optionally, the body 252 may include one or more mounting features 251, such as openings provided at opposite ends thereof. The mounting features 251 receive a mating component on the instrument to position the inspection apparatus 250 at a desired location. In the example of FIG. 1C, the mounting features 251 represent holes that receive corresponding pins. Alternative or additional mounting features may be utilized.

A general process for assembling the inspection apparatus 250 will be described. The optical target 270 is inserted into the pocket 264. In the example of FIG. 1C, opposite ends of the pocket 264 include cavities 263 that facilitate introduction of an adhesive. For example, a tool (e.g., a syringe) loaded with adhesive may be inserted into the cavities 263 at the ends of the optical target 270. Adhesive is introduced from the tool and allowed to wick/flow, through capillary force, along the bottom surface of the optical target 270 at least partially across bottom pocket ledges 259. Capillary forces pull the optical target 270 against the bottom of the pocket ledges 259, thereby maintaining the optical target 270 at a desired depth within the pocket 264. Optionally, when the adhesive represents a UV cured adhesive, UV light may be introduced at this point to cure the adhesive.

The grating layer 272 is loaded into the inset region 268, with a perimeter of the inset region 268 abutting against an exterior perimeter of the grating layer 272. The body 252 includes one or more cavities 249 about the perimeter of the inset region 268 such that, once the grating layer 272 is positioned in place, the cavities 249 are distributed about a perimeter of the grating layer 272. Once the grating layer 272 is mounted into the inset region 268, an adhesive dispensing tool (e.g., a pneumatic adhesive dispenser loaded with a syringe) may be utilized to introduce a controlled amount of adhesive at one or more points about the perimeter of the grating layer 272. For example, a tip of a syringe may be inserted into the cavities 249 at corners of the grating layer 272. A predetermined amount of adhesive is introduced. The adhesive is pulled, through capillary forces, along the interface between the grating layer 272 and the exterior ledge 269. The capillary force causes the adhesive to wick/flow along the outer edge 269, without flowing over the portion of the grating layer 272 proximate to the optical target 270. The capillary forces pull the grating layer 272 against the exterior ledge 269, thereby maintaining the grating layer 272 at a desired depth within the inset region 268. Optionally, when the adhesive represents a UV cured adhesive, UV light may be introduced at this point to cure the adhesive.

Additionally or alternatively, adhesive may be introduced onto the interior ledge 265. The adhesive may be introduced to the interior ledge 265 before or after the grating layer 272 is inserted into the inset region 268. For example, one or more drops of adhesive may be located on the interior ledge 268 before the grating layer 272 is inserted. Optionally, an adhesive dispensing tool may be utilized to introduce adhesive to the interior ledge 265 after insertion of the grating layer 272. For example, a tip of a syringe may be inserted through one or more of the inlet/outlet ports 267, and the syringe may introduce a predetermined amount of adhesive. The adhesive is pulled, through capillary forces, along the interface between the grating layer 272 and the interior ledge 265. The capillary force causes the adhesive to wick/flow along the interior ledge 265, without flowing over the portion of the grating layer 272 proximate to the optical target 270. The capillary forces pull the grating layer 272 against the interior ledge 265, thereby maintaining the grating layer 272 at a desired depth within the inset region 268. Optionally, when the adhesive represents a UV cured adhesive, UV light may be introduced at this point to cure the adhesive.

An adhesive (e.g., silicone) is introduced into the channel 266 through one or more of the inlet/outlet ports 267. For example, the inlet/outlet ports 267 at one or more corners of the channel 266 may be utilized as an inlet to introduce adhesive, while the inlet/outlet ports 267 at one or more other corners of the channel 266 form an outlet to allow air to discharge from the channel 266. As explained above, as the adhesive flows through the channel 266, and the adhesive bridges over the pockets 271. The pockets 271 later provide an air relief for shrinkage as the adhesive is cured.

Figure 2A:
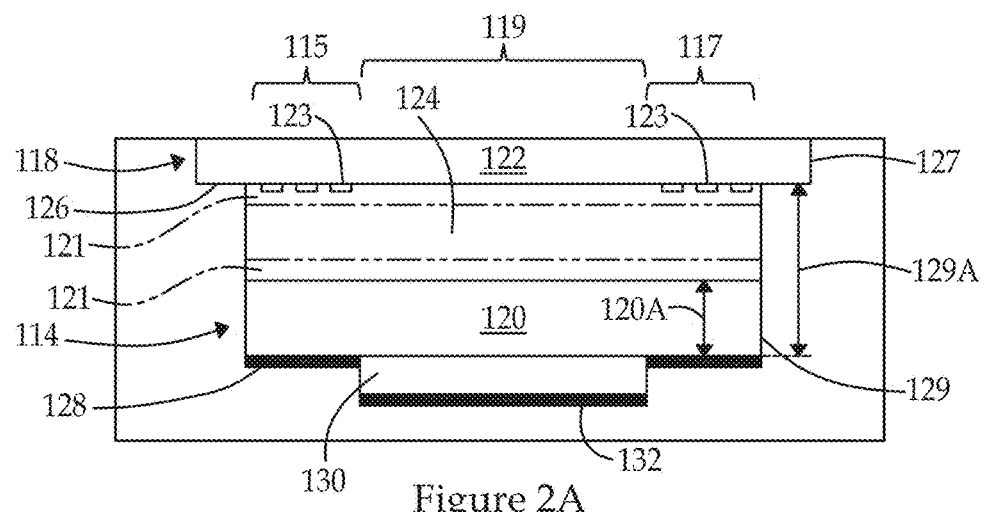
FIG. 2A illustrates a side sectional view of the inspection apparatus of FIG. 1A along line 2A-2A in FIG. 1A, with the optical target installed in accordance with examples herein.

FIG. 2A illustrates a side sectional view of the inspection apparatus 100 of FIG. 1 along line 2A-2A in FIG. 1, with the optical target 120 installed. FIG. 2A illustrates the optical target 120 installed in the pocket 114, and a transparent layer, representing a grating layer 122, mounted in the inset region 118. The grating layer 122 may have different regions to be used in connection with different types of alignment operations and/or calibration tests. For example, as discussed below in connection with FIG. 2D, the grating layer 122 may include one or more "tiles", representing regions at which the objective (200 in FIG. 2D) is positioned to collect information in connection with various operations. By way of example, the grating layer 122 may include one or more image quality tiles, distortion tiles, clear tiles, fiducials and the like. The objective is positioned relative to various tiles to collect information in connection with performing various tests. The grating layer 122 may also be used to monitor the uniformity and position of the excitation spatial profile. The grating layer 122 may be formed from a clear carrier substrate (e.g., glass) with various microstructures 123 provided thereon and shaped in one or more predetermined patterns. The microstructures 123 are provided in one or more tiles/areas, at which the objective is positioned in connection with corresponding calibration operations and tests. Examples of various calibration operations and tests are described below in connection with FIG. 10. For example, the microstructure 123 may comprise chromium or another opaque composition, where the composition exhibits a desired amount of opacity (e.g., partially or entirely opaque) to excitation light and/or one or more fluorescence emission bands of interest. For example, a layer of chromium may be deposited through various techniques onto the surface of the grating layer 122, with different regions of the chromium forming different patterns (also referred to as "chrome" or a "chrome pattern") to be utilized in connection with different alignment and/or calibration operations as described herein. The microstructure 123 may be shaped with various patterns, such as strips, dots, pinholes and the like. Optionally, the microstructure 123 may be provided as a solid layer with the predetermined pattern represented by opening or gaps through the microstructure 123 that form channels, pin holes, and the like. The microstructure 123 may be provided on an upper and/or lower surface of the grating layer 122, where the upper and lower surfaces are designated relative to the objective of the instrument. For example, the upper surface represents the surface that is proximate to the objective, while the lower surface represents the surface that is distal from the objective. Alternately, the grating structure may be patterned directly on the solid fluorescing substrate (e.g., see FIG. 2E) to form a monolithic structure. In this example, the grating structure is in contact with the optical target 120 which increases the coupling of the excitation illumination to the optical target and likewise increases the coupling of the fluorescence of the optical target 120 to the grating structure such that the light intensity emitted achieves a desired level (e.g., is maximized). Optionally, the grating layer 122 may be omitted entirely. Optionally, a spacing between the grating layer 122 and optical target 120 may be adjusted to provide for spherical aberrations.

In the example shown in FIG. 2A, the microstructure 123 includes first and second grating regions 115, 117 that are separated by a central region 119. The central region 119 is void of microstructures 123.

As shown in FIG. 2A, an anti-reflective coating 121 may be formed on a surface of at least one of the transparent layer (grating layer 122) or the optical target 120. The anti-reflective coating 121 may be formed on any surface that faces a fringe gap between the grating layer 122 and the optical target 120. In one example, the anti-reflective coating 121 is positioned on the surface of the optical target 120. In another example, the anti-reflective coating 121 is positioned on the surface of the grating layer 122, including on the microstructures 123. In yet another example, the anti-reflective coating 121 is positioned on the surface of the optical target 120 and on the surface of the grating layer 122, including on the microstructures 123.

To form one example of the anti-reflective coating 121, an anti-reflective material may be applied to the surface of the optical target 120 that is to face the fringe gap 124 when the optical target 120 is positioned in the pocket 114. To form another example of the anti-reflective coating 121, the microstructures 123 may be formed on the surface of the transparent layer (i.e., grating layer 122), and then the anti-reflective material may be applied to the surface.

The anti-reflective coating(s) 121 may be included to reduce or eliminate optical interference that may occur from light reflecting between the surface of the optical target 120 and the grating layer 122 in the fringe gap 124. As a result, optical interference patterns or fringes may be reduced or eliminated from images that are obtained when using the apparatus and device disclosed herein.

While the anti-reflective coatings 121 are shown as single layers, it is to be understood that a single layer may be used or multiple layers may be used to achieve the desirable anti-reflective effect. For example, multiple layers may be stacked up in order to achieve minimal or no reflection at the emission band/wavelength(s) of interest. For example, a multi-layer anti-reflective coating 121 may exhibit from 0% reflectance to 1% reflectance at wavelengths ranging from about 520 nm to about 700 nm, and may exhibit from 0% reflectance to about 5% reflectance at wavelengths ranging from about 500 nm to about 520 nm, and may also exhibit from 0% reflectance to about 9% reflectance at wavelengths ranging from about 700 nm to about 1000 nm. As such, the anti-reflective properties of the anti-reflective coating(s) 121 may not be the same for different wavelengths, and may be varied depending upon the application in which the apparatus or device is being used.

Examples of suitable anti-reflective materials that may be used to form the anti-reflective coating(s) 121 include any transparent material having a refractive index equal to the square root of the refractive index of the substrate (e.g., optical target 120 or grating layer 122) on which the material is placed. Some examples of anti-reflective materials include magnesium fluoride ($MgF_2$), fluoropolymers, mesoporous silica nanoparticles, alternating layers of silica and a higher refractive index material, or other anti-reflective materials that exhibit the desirable anti-reflective property within the desirable emission band/wavelengths being used.

In the present example, the inset region 118 is formed with an inset ledge 126 and inset wall 127 that are formed in the body 102. The inset ledge 126 is spaced a predetermined distance below the top surface 104 of the body 102 and extends inward by a predetermined distance. The inset ledge 126 defines a depth of the inset region 118, where the depth corresponds to a thickness of the grating layer 122. For example, the inset ledge 126 may extend inward by a distance sufficient to support the grating layer 122. As one example, an adhesive may be applied along the inset ledge 126 to retain the grating layer 122 in a desired position. The inset ledge 126 may have a length that is determined in part to allow the adhesive to spread across the inset ledge 126 without overflowing into the pocket 114. The ledge wall 127 is shaped and dimensioned to extend about a perimeter of the inset region 118. The inset region 118 is formed continuous with the pocket 114.

The pocket 114 is bordered and defined by a pocket ledge 128 and a pocket wall 129. The pocket ledge 128 is spaced a predetermined distance below the inset ledge 126 and extends inward by a predetermined distance. For example, the pocket ledge 128 may extend inward by a distance sufficient to support the optical target 120. As one example, an adhesive may be applied along the pocket ledge 128 to retain the optical target 120 in a desired position. The pocket ledge 128 may extend inward by a length that is determined in part to allow the adhesive to spread across the pocket ledge 128 without overflowing into a diffusion well 130. The pocket 114 is spaced apart inward within the body 102 such that the pocket 114 is centered in the body 102 to prevent the adhesive from getting under the central region 119 of the optical target 120.

The pocket wall 129 is shaped and dimensioned to correspond to a shape of the optical target 120. The pocket wall 129 has a height that extends from the pocket ledge 128 to the inset ledge 126. The height 129A of the pocket wall 129 is a predetermined distance greater than a height 120A of the optical target 120 such that, when the optical target 120 is inserted and firmly rests against the pocket ledge 128, a top surface of the optical target 120 is located below a plane of the inset ledge 126. The top surface of the optical target 120 is located below the plane of the inset ledge 126 by a thickness of a fringe gap 124. The fringe gap 124 corresponds to a distance between the top surface of the optical target 120 (or an anti-reflective coating 121 thereon) and a bottom surface of the grating layer 122 (or an anti-reflective coating 121 thereon). The fringe gap 124 is large enough to avoid interference fringes. Interference fringes may occur when the grating layer 122 and the optical target 120 directly contact one another at one or more points. The fringe gap 124 is sufficiently large to avoid direct contact between the optical target 120 and the grating layer 122. The fringe gap 124 is small enough to avoid introducing adverse optical properties as light passes between the grating layer 122 and the optical target 120. For example, if the fringe gap 124 were made unduly large, an excessive amount of light may be lost while passing through the fringe gap 124. The fringe gap 124 avoids undue loss of light within the fringe gap 124 as the light passed between the grating layer 122 and optical target 120. For example, the fringe gap 124 may have a thickness of or between about 10 µm and about 100 µm, and, in an example, a thickness of about 30 µm (+/−20 µm). Optionally, the fringe gap 124 may have a different thickness provided that an amount of light loss remains within a predetermined light loss limit (e.g., less than or equal to about 20% of the incoming light intensity). Optionally, the grating layer 122 and the optical target 120 may experience a controlled minimal amount of contact which may introduce small interference fringes that do not unduly affect use of the optical target 120. As mentioned above, the interference fringes may be further reduced or eliminated by including the anti-reflective coating 121 on one or both of the optical target 120 and the grating layer 122.

Optionally, an index matching fluid or index matching epoxy may be provided to fill the fringe gap 124 to reduce the potential for movement between the grating layer 122 and the optical target 120 over time. At least certain index matching epoxies may experience slight changes in color (e.g., discoloration) over time which may be undesirable in at least certain applications. Also, a potential exists that an index matching fluid may leak out of the fringe gap 124 over time. Consequently, the potential exists that, at least certain index matching fluids and/or epoxies may cause the intensity of the fluorescence emission to change over time. For example, over time the matching fluid or epoxy may slightly diminish the excitation light intensity impinging upon the optical target 120 and/or the intensity of the fluorescent emission that crosses the fringe gap 124. Accordingly, in at least certain examples, utilizing air within the fringe gap 124 may represent at least one aspect for maintaining a constant intensity of the fluorescence emitted from the inspection apparatus 100. Further, the addition of an index matching fluid or epoxy may introduce an extra step/complexity to the manufacturing process that is not otherwise present when the fringe gap 124 is filled with air.

The pocket 114 is joined with a diffusion well 130 located below the pocket 114 (distal from the objective 200, shown in FIG. 2B), and below the optical target 170 when inserted in the pocket 114. The diffusion well 130 is located below the pocket 114 and is centered within the optical target 120. The diffusion well 130 is configured to receive light that passes through the optical target 120. The light progressively becomes defocused or diffused as the light traverses the diffusion well 130 until contacting a well base 132. When the light engages the well base 132, the light has diffused to a desired degree sufficient to avoid photo bleaching of the well base 132.

The pocket 114 has a height that is dimensioned to provide a desired distance (e.g., a maximum distance) between a focal point of the light (within the optical target 120) and a bottom portion of the body 120. The diffusion well 130 includes a well bottom 132 that may be provided with a pigment-based black finish or coating to facilitate avoidance of photo bleaching and to manage reflectivity to within a desired level (e.g., less than or equal to about 6%). For example, the pigment-based black finish may represent an electrolytic blackening using inorganic metallic salts such as ANOBLACK™ EC offered by Anoplate Corp. of Syracuse, N.Y. In accordance with examples disclosed herein, the black finish is provided utilizing a pigment, and not a dye, as black dyes have large molecules (relative to the molecule size for pigments) that are more susceptible to being broken down over time with exposure to the excitation light. The pigments, utilized to form the black finish, in accordance with at least some examples, are formed from smaller molecules that are less susceptible to the excitation light and are not broken down over time. As one example, the pigment may be phosphorous enriched black nickel oxide which forms a black finish, has a relatively small molecule size that is not susceptible to being broken down by excitation light and thus maintains a relatively constant reflectivity. Also, the pigment may be chosen to afford low fluorescence in the coating because a low initial fluorescence in the coating will mean that the coating fluorescence will not drop by much over time.

Optionally, various other portions of the surface of the body 102 (e.g., the top and/or bottom surfaces 104, 106, the lateral sides 108 and/or front and back ends 110, 112 may be covered with the finish or coating.

Figure 2B:
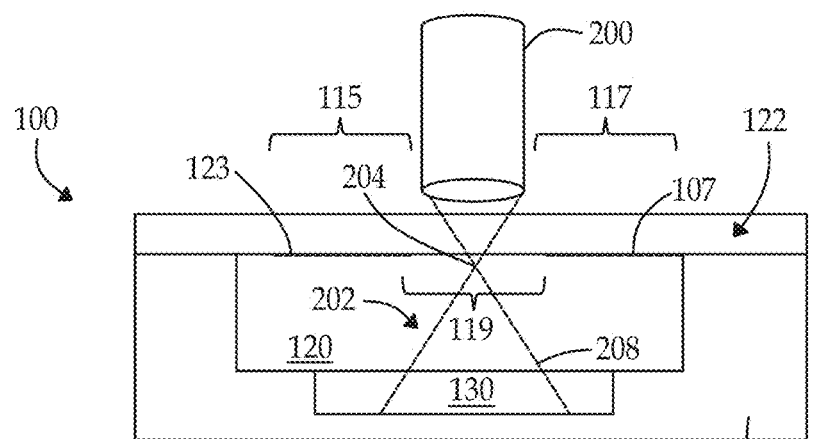
FIG. 2B illustrates a side view of a model of the optical target with an objective positioned at a first measurement position in accordance with an example herein.
Figure 2C:
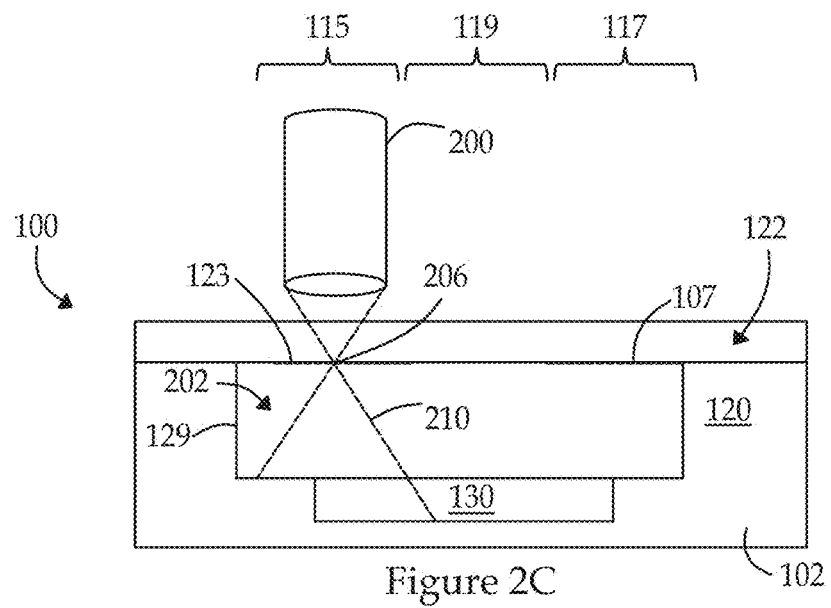
FIG. 2C illustrates a side view of a model of the optical target with the objective positioned at a second measurement position in accordance with an example herein.

FIG. 2B illustrates a side view of a model of the optical target 120 with an objective 200 positioned at a first measurement position in accordance with an example herein. FIG. 2C illustrates a side view of a model of the optical target 120 with the objective 200 positioned at a second measurement position in accordance with an example herein. FIGS. 2B and 2C illustrate the objective 200 positioned at first and second measurement locations, respectively, relative to the inspection apparatus 100. The models of FIGS. 2B and 2C illustrate the body 102, optical target 120, grating layer 122, and diffusion well 130, among other structures, although to simplify the illustration, the fringe gap 124 and other features of FIG. 2A are not illustrated in detail.

In FIG. 2B, the inspection apparatus 200 is positioned proximate the central region 119 of the grating layer 122, such as in connection with performing excitation measurement operations. When the objective 200 is positioned within the central region 119, the excitation light 202 avoids the microstructures 123 in the grating regions 115, 117. The objective 200 directs excitation light 202 into the inspection apparatus 100, where the excitation light 202 is focused to different focal points based upon the particular measurement being performed. For example, in connection with the frame measurement operation (corresponding to FIG. 2B), the objective 200 focuses the excitation light 202 to a focal point 204 that is below the upper surface 107 of the optical target 120 (e.g., 50 µm). The objective 200 manages an angular aperture 208 to obtain a desired degree of focus at the focal point 204 and to obtain a desired degree of diffusion/defocus at greater depths within the optical target 120 and thereafter. The objective 200 receives fluorescence emission that is emitted from the upper surface 107 of the optical target 120 within the central region 119.

During operation, non-grating-based measurements (e.g., an optical intensity measurement) may be obtained by positioning the objective 200 above the region 119. For example, the non-grating-based measurement may be performed in connection with imaging the position of the excitation light illumination relative to a field of view of a detection camera. The focal point 204 is located below the upper surface 107 in order to remove scratches, dust, fingerprints and the like from the focal plane, such as debris, scratches and defects in the surface of the optical target 120, so that these potentially interfering effects will have no or relatively little affect on the measurement. Other operations are discussed in connection with FIG. 10 that may utilize images obtained from the region 119.

Excitation light is emitted from the objective 200, and travels through the grating layer 122 and into the optical target 120 without passing through the microstructures 123. In response, the optical target 120 produces fluorescence emissions from within the optical target 120 that return through the region 119 and impinge upon the objective 200, where the fluorescence emissions are redirected through internal optics to one or more detectors. The objective 200 focuses the excitation light at a focal point that is located below a surface of the optical target 120 by a predetermined distance. For example, the focal point 204 may be located from about 20 µm to about 100 µm below the surface 107 of the optical target 120. As another example, the focal point 204 may be located at about 50 µm below the surface 107 of the optical target 120. The excitation light is diffused within a lower portion of the optical target 120 below the focal point 204 to cause fluorescence emission across a relatively large area within the optical target 120, thereby affording a relatively uniform scan. At least some examples eliminate or substantially reduce negative effects of scratches, debris, fingerprints and the like on the surface 107 of the optical target 120 and/or grating layer 122 by locating the focal point 204 below the surface 107 of the optical target 120 and managing the angular aperture 208.

In FIG. 2C, the inspection apparatus 200 is positioned proximate to one of the grating regions 115, 117, such as in connection with performing a grating measurement operation. When the objective 200 is positioned proximate to one of the grating regions 115, 117, the excitation light 202 impinges upon the microstructures 123, passing through gaps or apertures therebetween. The objective 200 focuses the excitation light 202 to a focal point 206 that corresponds to the bottom surface of the grating layer 122. The objective 200 manages an angular aperture 210 to obtain a desired degree of focus at the focal point 206 and to obtain a desired degree of diffusion/defocus at greater depths within the optical target 120 and thereafter. The focal point 206 also corresponds to the position of the microstructures 123. The objective 200 receives fluorescence emission that is emitted from the optical target 120 within a corresponding grating region 115, 117. In accordance with at least some examples, all or a portion of the emission may come from a top volume of the optical target 120, while none or a lesser portion of the emission comes from the remaining volume of the optical target 120.

During operation, grating-based measurements are obtained by positioning the objective 200 above one or both of the first and second grating regions 115 and 117. Excitation light is emitted from the objective 200, travels through the grating regions 115, 117 and into the optical target 120. The excitation light diffuses or defocuses beyond the focal point 206 at a rate determined by the angular aperture 210 at greater depths within the optical target 120. In response to the excitation light, the corresponding region of the optical target 120 produces fluorescence emissions that emit from the upper surface 107 and impinge upon the lower surface (and microstructures 123) of the grating layer 122. The fluorescence emissions pass between the microstructures 123 on the grating layer 122 and pass upward until impinging upon the objective 200. The fluorescence emissions are redirected through internal optics to one or more detectors and are processed accordingly. To the extent that excitation light passes through the optical target 120, the excitation light exhibits a desired degree of defocus when passing through the diffusion well 130 before contacting the well bottom 132. The intensity of the excitation light that contacts the well bottom 132 is below a predetermined threshold and as such, avoids a potential of changing the optical characteristics of the well bottom 132 over time.

As the excitation light passes beyond the microstructures 132, the laser light diverges into a larger area which causes a relatively large portion of the optical target 120 to glow when emitting fluorescence. Accordingly, cameras within the instrument are able to collect chrome pattern measurements from portions of the microstructures 132 that may be positioned laterally to either side of the focal point 206, thereby affording improved illumination uniformity for the chrome pattern measurements.

The objective 200 may be provided with a large numerical aperture, such that, the further the objective 200 is moved away from the surface of the grating layer 122, the more out of focus the excitation source becomes. The excitation laser diverges as the excitation light moves away from the focal point 206. The rate, at which the excitation light diverges/focuses, is dependent in part on the numerical aperture of the objective 200. In accordance with at least some examples, the excitation light is substantially defocused by the time the excitation light exits the bottom surface of the optical target 120. The excitation light continues to further diverge (become more unfocused) as the excitation light passes the diffusion well 130. By the time the excitation light impinges upon the well bottom 132, the excitation light is defocused/divergent to a desired degree to limit the intensity of energy impinged upon any point on the well bottom 132 to below a desired intensity threshold.

In accordance with the examples herein, the objective 200 and inspection apparatus 100 avoid undue photo degradation of the body 102 (e.g., minimize the photo bleaching) by spreading the excitation laser lines over a large area (e.g., 2.3 mm in X and 0.53 mm in Y). In addition, some examples avoid undue auto-fluorescence (e.g., minimize) of structures on the body 102, in part, by managing focus of the excitation light such that the excitation light is defocused by a desired amount (measured at less than about 1.5% of the Er—InF$_3$ signal) when the excitation light impinges upon surfaces of the body 102.

In addition, the diffusion well 130, and the distance between the focal point 206 and the well bottom 132, reduce a potential for auto-fluorescence. Auto-fluorescence may result from the well bottom 132 in response to reception of excitation light. To the extent that the well bottom 132 emits any fluorescent energy, such fluorescent energy becomes substantially dispersed while traveling through the diffusion well 130 without impacting the characteristics of interest from the optical target 120.

Optionally, in accordance with at least some examples, a length of the optical target 120 may be dimensioned in a desired manner relative to the microstructures 123 within the grating regions 115, 117. For example, it may be desirable to manage the position of the objective 200 such that, when performing the measurements over the grating (corresponding to FIG. 2C), the excitation light within the numerical aperture 210 does not impact the pocket wall 129.

In accordance with examples herein, the inspection apparatus 100 affords a fluorescent source that substantially remains constant over a large period of time. For example, the inspection apparatus 100 does not exhibit notable loss of fluorescence intensity and remains substantially stable over at least 10,000 inspection operations (where each inspection operation corresponds to at least one illumination operation of the optical target by excitation light). As another example, the inspection apparatus 100 may exhibit no more than about a 3% change in fluorescence emission intensity over at least 10,000 inspection operations. More generally, the inspection apparatus 100, when formed in accordance with examples described herein, exhibits no more than about a 2% reduction in fluorescence emission intensity over a useful life of a corresponding instrument with which the inspection apparatus 100 is utilized.

Figure 2D:
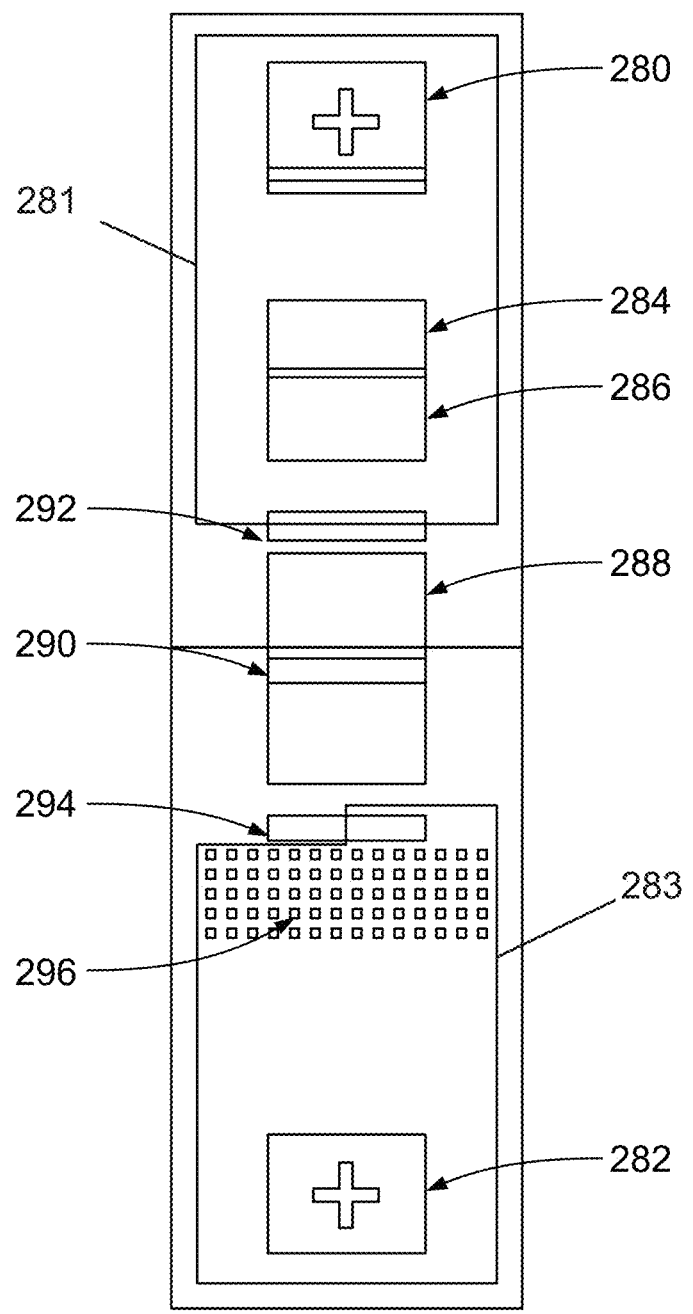
FIG. 2D illustrates a top plan view of the inspection apparatus formed in accordance with an example.

FIG. 2D illustrates a top plan view of the inspection apparatus formed in accordance with an example. The grating layer (122 in FIG. 2A) and microstructures are arranged in various tiles/areas to be utilized in connection with different types of test. The regions within the boxes labeled 281 and 283 in FIG. 2D (including any sub-regions identified within boxes 281 and 283) correspond to areas where chrome/microstructures is/are provided on the grating layer. It is to be understood that these areas may also be chrome with pinholes. Any region outside of the regions marked 281 or 283 (e.g., the region between 281 or 283 and the perimeter, or between 281 and 283) represent clear areas where no chrome/microstructures are positioned. It is to be understood that the area within the plus signs may also be clear areas where no chrome/microstructures are positioned.

The inspection apparatus includes top and bottom auto centering fiducials 280, 282 that are utilized in connection with an automated centering operation for an imaging apparatus. An image quality tile 284 is provided for use with an image quality test. A distortion tile 286 is provided to be utilized in connection with a distortion test. A clear tile 288 is provided for use with an illumination uniformity and flat field correction operation. A clear area 290 is provided for use with laser line measurements. A horizontal knife edge 292 and a vertical knife edge 294 are provided in connection with laser spot position checks. A pattern of clear holes is provided at tile 296 to be utilized in connection with measuring a modulation transfer function. Optionally, additional, fewer or alternative tile areas may be provided.

Figure 2E:
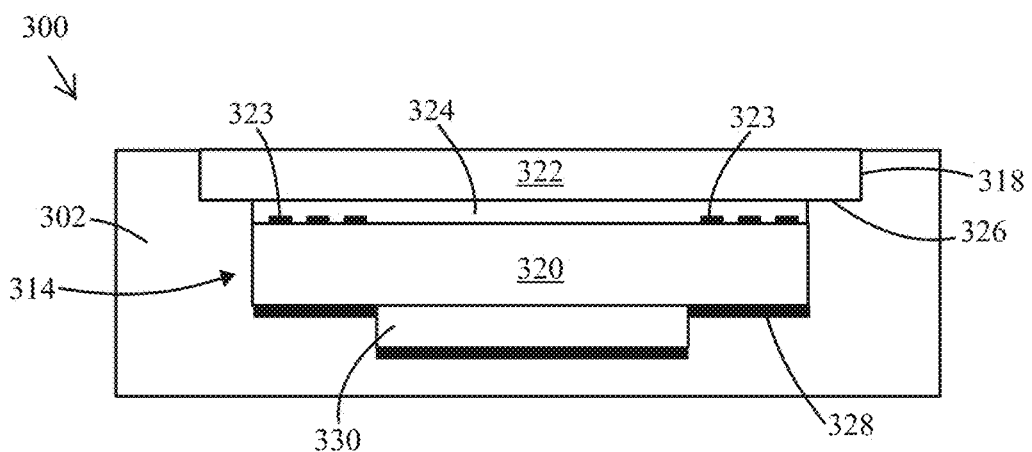
FIG. 2E illustrates a side sectional view of an inspection apparatus formed in accordance with an alternative example.

FIG. 2E illustrates a side sectional view of an inspection apparatus 300 formed in accordance with an alternative example. The inspection apparatus 300 resembles the inspection apparatus 100 of FIG. 2A in various manners, with the differences discussed hereafter. The inspection apparatus 300 includes a body 302 that receives an optical target 320 in a pocket 314. The pocket 314 includes a pocket ledge 328 that maintains the optical target 320 above a diffusion well 330 and at a predetermined depth within the body 302. A transparent layer 322 (e.g., formed of glass) is inserted into an inset region 318 defined in the body 302. An exterior ledge 326 maintains the transparent layer 322 a predetermined distance above the optical target 320, with a fringe gap 324 therebetween. The optical target 320 includes microstructures 323 formed on the top surface thereof. The microstructures 323 are separated from the transparent layer 322 by the fringe gap 324. The microstructures 323 form a grating layer on a surface of the optical target 320 that is separate and distinct from the transparent layer 322. Optionally, the transparent layer 322 may be omitted entirely. Optionally, a spacing between the transparent layer 322 and optical target 320 may be adjusted to provide for spherical aberrations. Accordingly, the inspection apparatus 300 be made by printing the chrome pattern (microstructure 323) directly onto the top surface of the optical target 320 instead of on the bottom of the transparent layer 322.

While not shown, the example shown in FIG. 2E may also include the anti-reflective coating 121 on the surface of the transparent layer 322 that faces the fringe gap 324 and/or on the surface of the optical target 320 and on the microstructures 323 formed on the optical target 320. Any examples of the anti-reflective material(s) disclosed herein may be used in this example.

The thickness of the transparent layer 322 is set to compensate for spherical aberration in the imaging system. If the imaging system is designed with zero spherical aberration, then the transparent layer 322 may be omitted entirely and the chrome pattern would be printed on top of the optical target 320. If the imaging system has spherical aberration (since it is designed to look through a certain thickness of glass), then the transparent layer 322 would be used even if the chrome pattern is printed on the optical target 320. Optionally, the fringe gap 324 may be omitted entirely, such that the optical target 320 directly rest on and abuts against a top surface of the optical target 320.

Figure 2F:
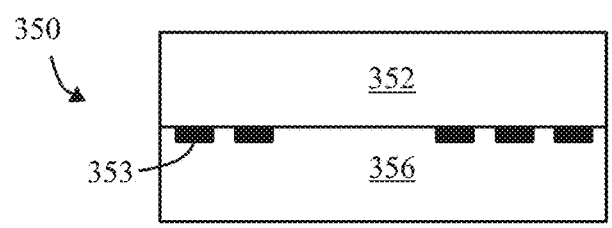
FIG. 2F illustrates a side sectional view of an inspection apparatus formed in accordance with an alternative example.

FIG. 2F illustrates a side sectional view of an inspection apparatus 350 formed in accordance with an alternative example. The inspection apparatus 350 does not include a separate body (such as the body 302 or body 102, described above). The inspection apparatus 350 includes an optical target 356 and a transparent layer 352 directly bonded onto one another. Microstructures 353 are provided at the interface between the optical target 356 and transparent layer 352. The microstructures 353 may represent one or more chrome patterns formed on a top surface of the optical target 356 and/or on a bottom surface of the transparent layer 352. By way of example, the inspection apparatus 350 may be utilized in examples in which the inspection apparatus 350 is located directly on a flow cell, instead of being mounted into an instrument. Additionally or alternatively, the inspection apparatus 350 may also be mounted within an instrument.

Optionally, the transparent layer 352 may be omitted entirely. For example, any of the optical targets 120, 320, 356 described herein may be utilized as a stand-alone inspection apparatus with no additional body components or transparent layers provided therewith. Optionally, the optical targets 120, 320 and 356 may be utilized as a stand-alone inspection apparatus with no microstructures or other patterns formed thereon or provided proximate thereto. For example, the optical targets 120, 320 and 356 may simply be mounted directly on a flow cell and/or within an instrument without any other supporting structures.

Figure 3A:
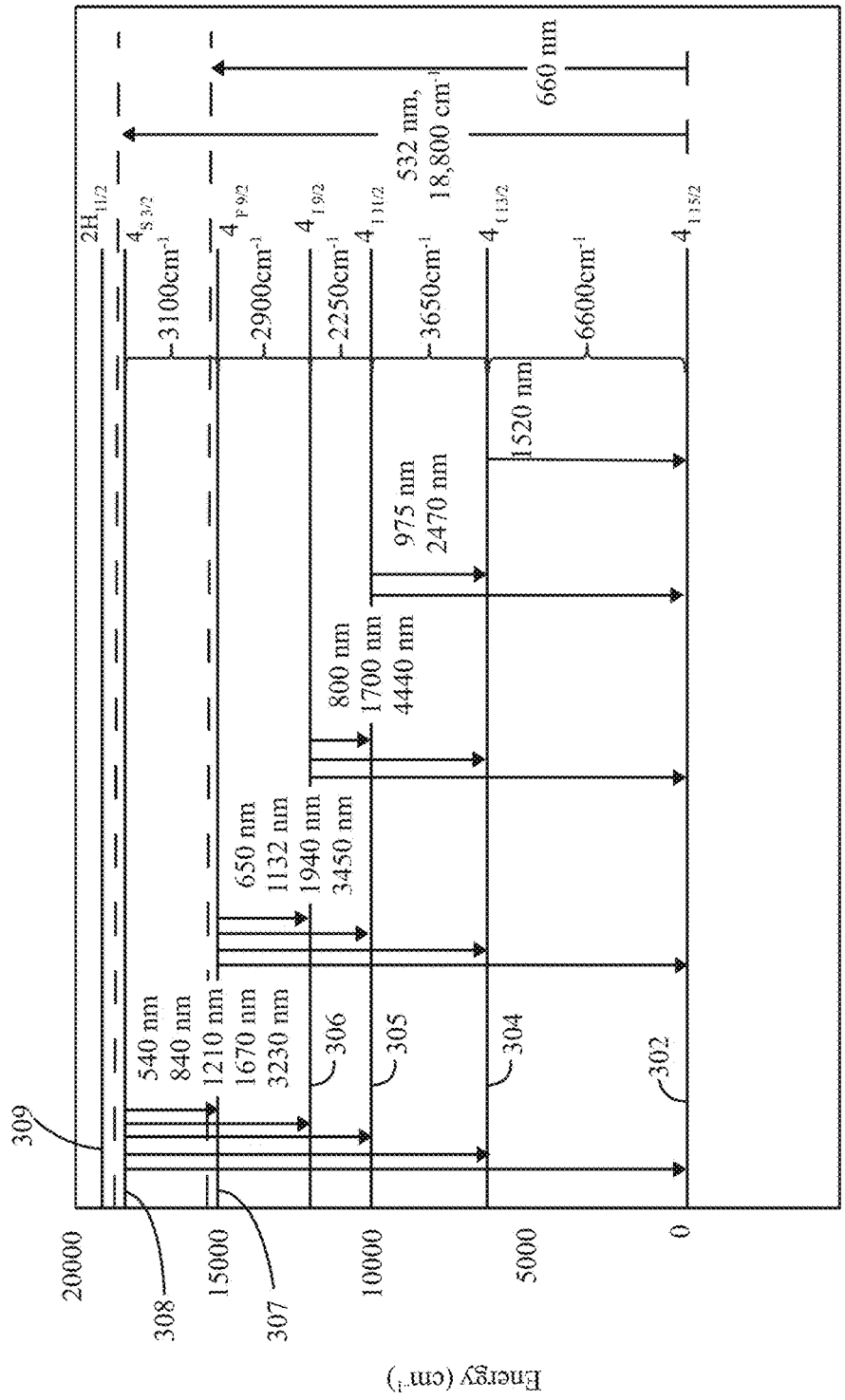
FIG. 3A illustrates an energy band diagram in connection with a trivalent erbium ion ($Er^{3+}$) utilized in accordance with examples herein.

FIG. 3A illustrates an energy level diagram in connection with a fluorescing material utilized in accordance with examples herein. The energy level diagram illustrates energy ($cm^{-1}$) along the vertical axis and alternative transitions distributed across the horizontal axis. A ground energy level 302 is illustrated, along with elevated energy levels 304-309, to which an electron of the trivalent erbium ion may be raised when excited. For example, an electron of the erbium ion may absorb an energy of about 18,800 cm$^{-1}$, causing the electron to move from the $^4I_{15/2}$ ground energy level 302 to a $^4S_{3/2}$ target excitation (TE) energy level 308. As another example, an electron of an erbium ion may absorb an energy of about 15,000 cm$^{-1}$, causing the electron to move from the $^4I_{15/2}$ ground energy level 302 to a different $^4F_{9/2}$ TE energy level 307. The electrons of the erbium ion absorb energy from the excitation light and then move to the corresponding TE energy level 307, 308. Once the ions have moved to a corresponding elevated TE energy level, the ions then discharge the absorbed energy, in the form of a photon, and return to the ground energy level 302. The TE energy level is separated from the ground energy level by a first energy gap $FM_{EGI}$ corresponding to a fluorescence emission wavelength of interest (FEWI). For example, the FEWI may be a red, green, blue or other emission wavelength. The discharged photon is then received by the objective as fluorescence emission. The color of the fluorescence emission is dependent upon the energy of the photon which corresponds to the first energy gap $FM_{EGI}$. When an ion transitions from the target excitation energy level 307 to the ground energy level 302, the corresponding discharged photon has an energy of about 15000 cm$^{-1}$ which is detectable as a fluorescence emission wavelength of interest of 650 nm (visible as a red fluorescence emission). When an ion transitions from the target excitation energy level 308 to the ground energy level 302, the corresponding discharged photon has an energy of about 18,800 cm$^{-1}$ which is detectable as a fluorescence wavelength emission of interest about 532 nm (visible as a green fluorescence emission).

FIG. 3A also illustrates additional energy level transitions that may be exhibited by a trivalent erbium ion. Each of the energy levels 304-308 has one corresponding next lower lying energy level. In accordance with examples herein, the solid host material and fluorescing material are chosen based in part on the energy gap between one or more target excitation energy levels (e.g., 308) and the next lower lying energy level (e.g., 307). The $^4F_{9/2}$ energy level 307 represents a next lower lying (NLL) energy level relative to the $^4S_{3/2}$ energy level 308. The $^4I_{9/2}$ energy level 306 represents the NLL energy level relative to the $^4S_{3/2}$ energy level 307.

Electrons may be elevated to the energy levels 304, 305 and 306, and when returning to the ground energy level 302 discharge photons having a corresponding amount of energy. The photons discharged during transitions from the energy levels 304-306 have corresponding wavelengths of 1520 nm, 975 nm and 800 nm, respectively. In addition, an electron may transition between intermediate elevated energy levels 304-308. When an electron transitions between adjacent or intermediate elevated energy levels, a photon is discharge with a corresponding amount of energy, which corresponds to the difference between the starting and ending elevated energy levels. FIG. 3A illustrates example wavelengths that may be visible in connection with photons emitted when electrons transition between different elevated energy levels. For example, an electron at the energy level 308 may transition to any of energy levels 307, 306, 305 and 304, in which case a discharged photon would have a wavelength of 3230 nm, 1670 nm, 1210 nm, and 840 nm, respectively. As a further example, when an electron at the energy level 307 transitions to another intermediate elevated energy level 306-304, the corresponding discharged photon will have a wavelength of 3450 nm, 1940 nm, and 1132 nm, respectively. The discharged photon will emit fluorescence at a color corresponding to the photon wavelength.

Several, but not all, examples described herein contemplate use of an inspection apparatus in connection with a fluidics system that utilizes fluorescence emissions in predetermined emission bands of interest. By way of example, the emission bands may be centered at a wavelength corresponding to a green fluorescence emission and/or corresponding to a red fluorescence emission. When the emission bands of interest are centered about wavelengths corresponding to red or green emissions, the corresponding portion of the energy diagram of FIG. 3A is of interest. More specifically, when green emission is of interest, it is desirable to transition between target excitation and ground energy levels 308 and 302. When red emission is of interest, it is desirable to transition between target excitation and ground energy levels 307 and 302. In the present example, transitions between other energy level combinations in the diagram of FIG. 3A are not of interest in connection with an instrument that utilizes red and/or green emission bands of interest.

It is recognized that the foregoing discussion is one example, and that other examples are contemplated as being within the purview of the instant disclosure. Additionally or alternatively, other emission bands may be of interest. For example, an instrument may utilize the emission band associated with 800 nm and/or 975 nm. When an emission band of interest has a wavelength centered about 800 nm and/or 975 nm, energy transitions between levels 306 and 302, and levels 305 and 302 are of interest. In general, energy bands above 1000 nm may typically not be of interest in connection with fluidics instruments, as the fluorescence emitted in connection with performing a sequencing analysis typically does not utilize energy bands above 1000 nm. Accordingly, the transition between the first elevated energy level 304 and the ground energy level 302 may not be of interest or useful in connection with a fluidics instrument.

In accordance with examples herein, fluorescence from the fluorescing material is achieved by optical excitation to an upper-lying energy level (also referred to as a target excitation energy level) by means of a laser or light emitting diode (LED) source. Following the optical excitation process, decay to lower lying energy levels within the impurity ion occurs via two competing energy transfer processes: radiative decay, with the corresponding emission of photons (fluorescence) and non-radiative decay, by means of optical phonon emission to the surrounding lattice structure. The non-radiative decay rate depends on the coupling interaction between the surrounding lattice and the impurity ion, dropping exponentially with the number of emitted phonons. Consequently, non-radiative processes involving a large number of emitted phonons have a low probability of occurrence. The non-radiative transition probability between two energy levels is adequately described by an exponential decaying function: $W_{mp}=C\exp(-\alpha\Delta E)[n(T)+1]^p$, where C and $\alpha$ are constants specific to the solid host material, $\Delta E$ is the energy gap separating the two energy levels, n(T) is the Bose-Einstein occupation number at temperature, T, and p is the minimum number of phonons required to span the energy gap. In general, non-radiative decay via multi-phonon processes can be minimized by selecting hosts with low maximum phonon energies. For example, to observe visible fluorescence at about 660 nm from the $Er^{3+}$ $^4F_{9/2}$–$^4I_{15/2}$ transition, it is necessary to minimize non-radiative decay between the $^4F_{9/2}$ level to the next lower lying state, $^4I_{9/2}$. Since the energy separation between the $^4F_{9/2}$–$^4I_{9/2}$ levels is ~2900 cm$^{-1}$, it is advantageous to select a host material with a maximum phonon energy less than or equal to about 580 cm$^{-1}$ (corresponding to the simultaneous emission of 5 or more phonons). In addition to favoring emission in the red wavelength region, selection of a low phonon host material also enhances green emission from the Er$^{3+}$ $^4S_{3/2}$ excited state, for which the next lower lying energy level ($^4F_{9/2}$) lies at about 3100 cm$^{-1}$ therebelow.

The solid host material has a predetermined phonon energy HOST$_{PE}$, while the fluorescing material exhibits a select ground energy level and a target excitation energy level separated from the ground energy level by a first energy gap corresponding to a fluorescence emission wavelength of interest (FEWI). In the example of FIG. 3A, the FEWI is the green and/or red emission wavelength. The fluorescing material has a next lower lying (NLL) energy level relative to the TE energy level. The NLL energy level is spaced a second energy gap FM$_{EG2}$ below the TE energy level wherein a ratio of the FM$_{EG2}$/HOST$_{PE}$ is three or more. Optionally, the ratio of the FM$_{EG2}$/HOST$_{PE}$ is at or between four and ten.

Figure 3B:
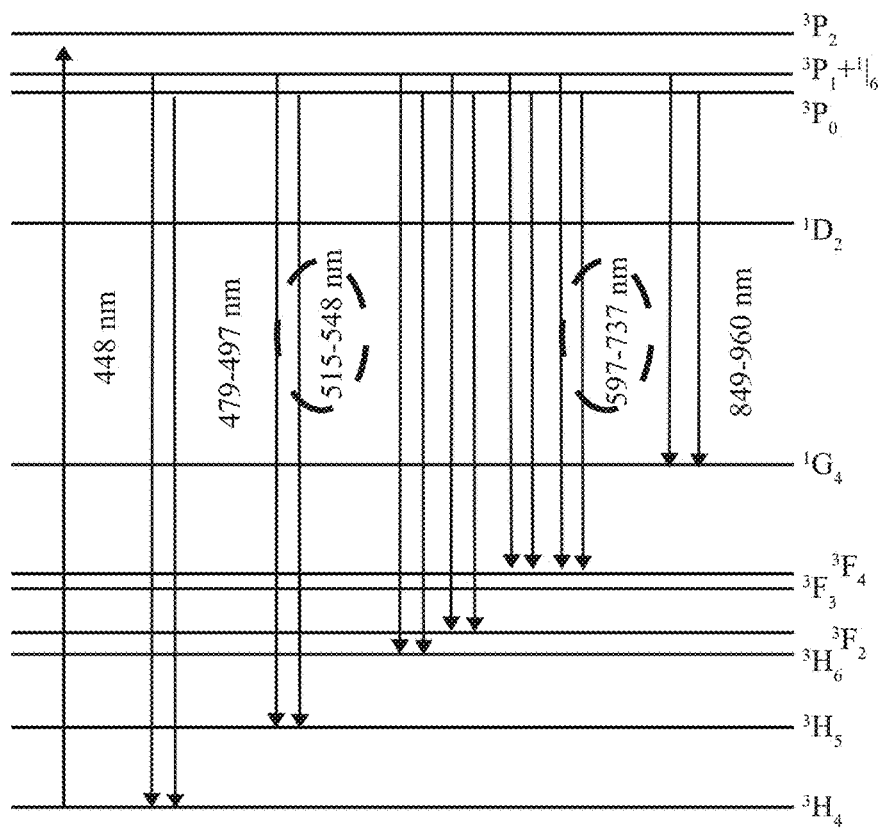
FIG. 3B illustrates an ion energy level diagram associated with a trivalent praseodymium ion ($Pr^{3+}$) in accordance with examples herein.
Figure 3C:
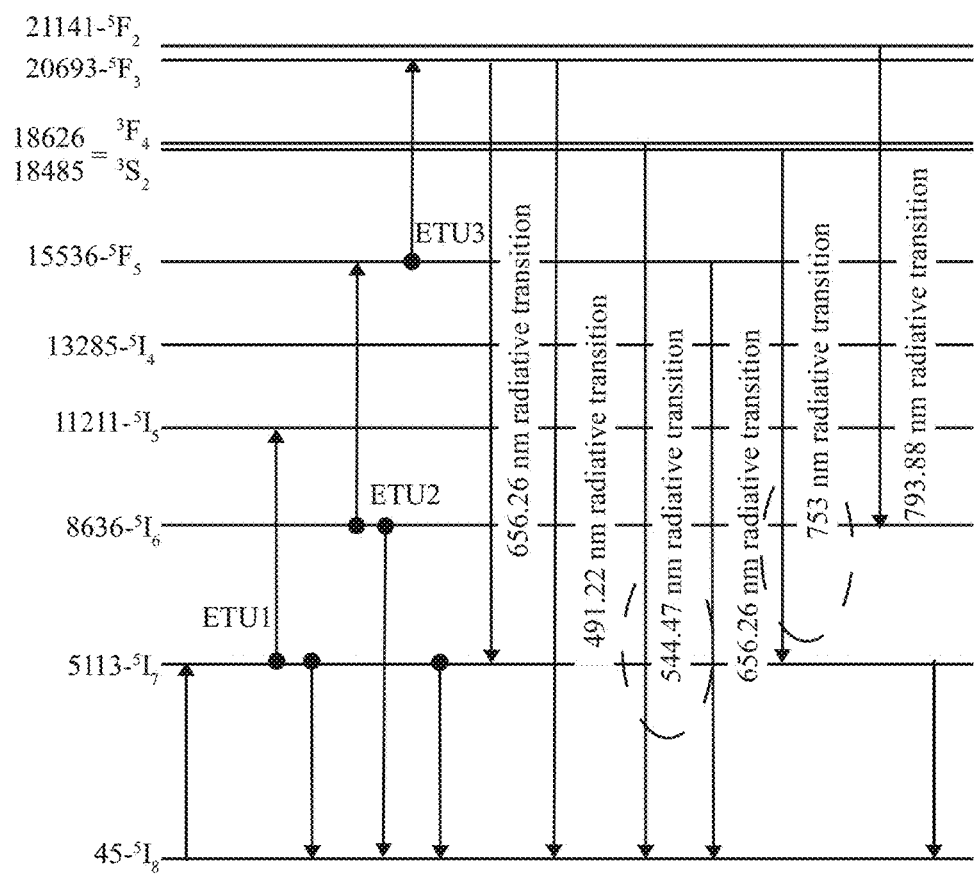
FIG. 3C illustrates an ion energy level diagram associated with a trivalent holmium ion ($Ho^{3+}$) in accordance with examples herein.

It is recognized that FIG. 3A represents one example of an energy level diagram associated with a potential fluorescing material that may be doped within a solid host material. As discussed herein, alternative fluorescing materials may be utilized as dopants. As examples, FIG. 3B illustrates an ion energy level diagram associated with a trivalent praseodymium ion (Pr3+), and FIG. 3C illustrates an ion energy level diagram associated with a trivalent holmium ion (Ho3+). The diagrams in FIGS. 3B and 3C illustrate ground energy levels, target excitation energy levels and intermediate elevated energy levels, as well as wavelengths associated with photons emitted by an electron when transitioning between the corresponding designated energy levels. Continuing with the foregoing example, the subset of the energy level transitions that is of interest is based on the emission band of interest.

With respect to Pr3+ (FIG. 3B), a transition between a target excitation energy level $^3P_0$ and ground energy level $^3H_5$ will emit a photon having a wavelength between 515 and 548 nm (which includes the band of interest at 532 nm). With respect to Pr$^{3+}$, a transition between target excitation energy level $^3P_0$ and intermediate energy level $^3F_4$ will emit a photon having a wavelength between 597 nm and 737 nm (which includes the band of interest at 660 nm). Accordingly, Pr$^{3+}$ may represent a potential candidate for a fluorescing material to be doped into a solid host material. In the example of FIG. 3B, when the target excitation energy level is $^3P_0$, the next lower lying energy level is $^1D_2$.

With respect to Ho$^{3+}$ (FIG. 3C), a transition between a target excitation energy level $^3F_4$ and ground energy level $^5I_8$ will emit a photon having a wavelength of about 544 nm (which is proximate to the wavelength band of interest at 532 nm). A transition between the target excitation energy level $^3S_2$ and intermediate energy level $^5I_7$ will emit a photon having a wavelength of about 656 nm (which is proximate to the band of interest at 660 nm). Accordingly, Ho$^{3+}$ may represent a potential candidate for a fluorescing material to be doped into a solid host material. In the example of FIG. 3C, when the target excitation energy level is $^3S_2$, the next lower lying energy level is $^5F_5$.

Figure 4:
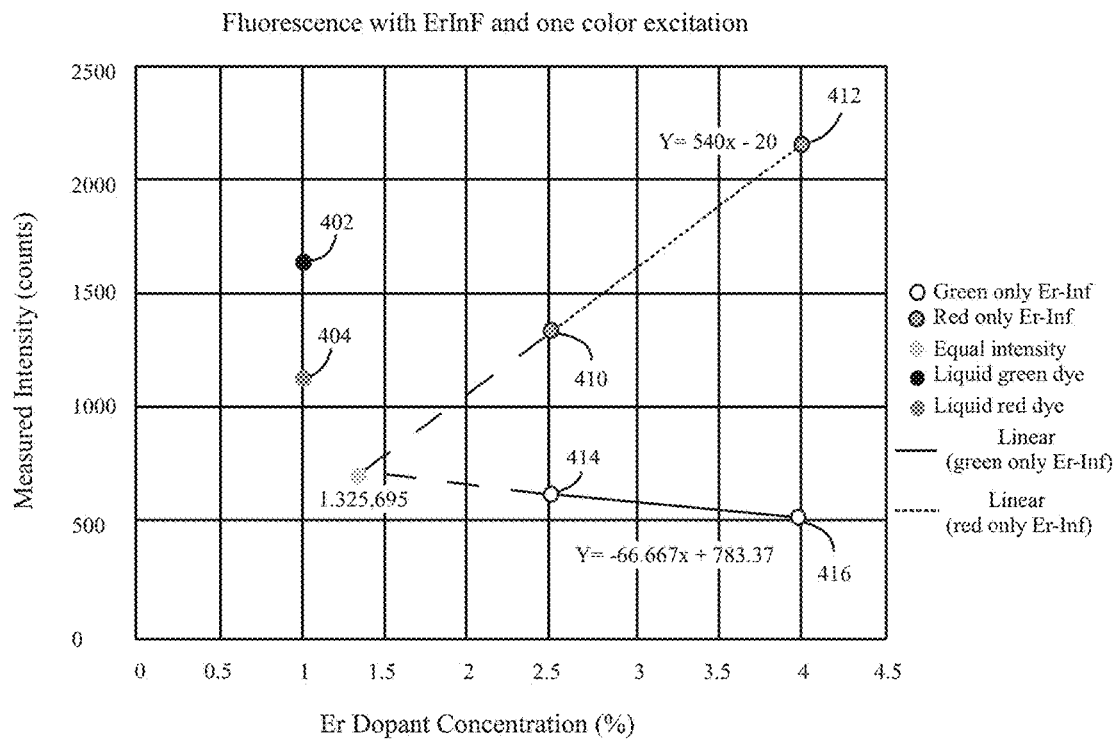
FIG. 4 illustrates example intensity test measurements corresponding to different fluorescence emission colors collected in connection with various optical targets in accordance with examples herein.

FIG. 4 illustrates an example of intensities that were exhibited for different fluorescence emission colors. The vertical axis plots energy intensity, while the horizontal axis plots a concentration (in percentage) of a fluorescing material doped into a solid host material. As reference points, data point 402 corresponds to an intensity measured upon excitation of a liquid green dye, while data point 404 corresponds to an intensity measured upon excitation of a liquid red dye. When the liquid green dye was illuminated with an excitation laser, the liquid green dye emitted fluorescence in the green energy spectrum with an intensity of about 1650 counts. When the liquid red dye was illuminated with an excitation laser, the liquid red dye emitted fluorescence in the red energy spectrum with an intensity of about 1150 counts.

FIG. 4 also illustrates data measurements performed in connection with solid-state optical targets, namely data points 410-416. Data points 410 and 414 correspond to the intensity measured upon excitation of a solid-state optical target in which a host indium fluoride glass was doped with a trivalent erbium ion at a concentration of 2.5%. Data points 412, 416 correspond to the intensity measured upon excitation of a solid-state optical target in which a host indium fluoride glass was doped with a trivalent erbium ion at a concentration of about 4%. As evident from FIG. 4, the 2.5% doped solid-state optical target emitted fluorescence in the green energy spectrum at about 650 counts and emitted fluorescence in the red energy spectrum at about 1300 counts. The 4.0% doped solid-state optical target emitted fluorescence in the green energy spectrum at about 500 counts and emitted fluorescence in the red energy spectrum at about 2350 counts. From the foregoing test data, concentrations of a trivalent erbium dopant can be determined, based upon the desired intensity of fluorescence. For example, when it is desirable for the optical target to emit fluorescence in the red energy spectrum, it may be desirable to increase the concentration of trivalent erbium ion dopant to 3.5% or more (e.g., 4%, 4.5%). When it is desirable for the optical target to emit fluorescence in the green energy spectrum, it may be desirable to decrease the concentration of trivalent erbium ion dopant to between about 1.5% and about 2%.

Figure 5:
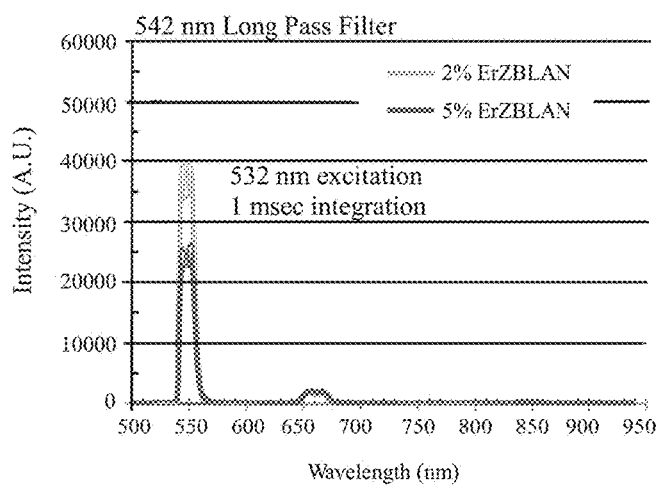
FIG. 5 illustrates test results of a solid host material that was formed by doping a metal fluoride glass (ZBLAN) with predetermined concentrations of a trivalent erbium ion in accordance with examples herein.

Further, from the foregoing test data, concentrations of a trivalent erbium dopant may be determined when it is desirable for the optical target to emit fluorescence in two or more energy spectrums with equal intensity (e.g., in the green and red energy spectrums). For example, it may be desirable to maintain the trivalent erbium ion dopant concentration between about 1.25% and about 2%. As a further example, a trivalent erbium ion dopant concentration may be between about 1.3% and about 1.5% within indium fluoride glass. FIG. 5 illustrates test results of a solid host material that was formed by doping a metal fluoride glass (ZBLAN) with about a 2% concentration and about a 5% concentration of a trivalent erbium ion. FIG. 5 plots an intensity along the vertical axis of fluorescence emissions and emission wavelength along the horizontal axis. The 2% concentration and the 5% concentration of erbium ions exhibited an intensity spike centered about 550 nm. The 2% and 5% erbium concentrations also exhibited a secondary intensity spike at about 660 nm.

In the example of FIG. 4, trivalent erbium ions represent an active fluorescing material. Optionally, one or more additional elements may be added as a co-dopant to the solid host material. The co-dopant may be utilized to increase or decrease the emission intensity of the active fluorescing material (e.g., erbium).

Figure 6A:
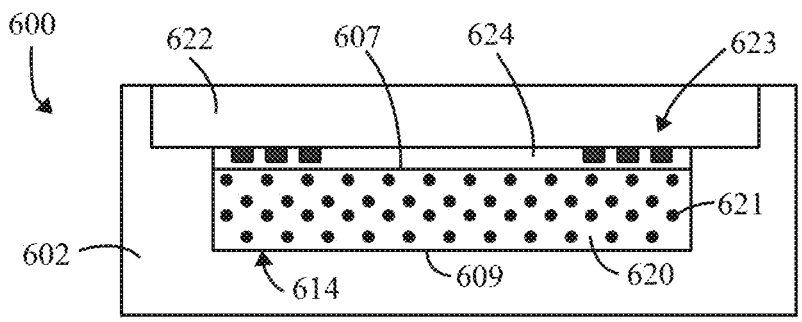
FIG. 6A illustrates a side sectional view of an inspection apparatus formed in accordance with an alternative example.

FIG. 6A illustrates a side sectional view of an inspection apparatus 600 formed in accordance with an alternative example. The inspection apparatus 600 includes a body 602 that holds an optical target 620 in a pocket 614. A grating layer 622 is positioned above the optical target 620 proximate to an objective (not shown). The grating layer 622 includes microstructures 623 formed in predetermined patterns on a bottom surface of the grating layer 622.

The optical target 620 may be separated from the grating layer 622 by a fringe gap 624. The optical target 620 includes top and bottom target surfaces 607, 609 that are generally planar and oriented parallel to one another. The optical target 620 comprises a solid body that includes a plurality of quantum dots 621 embedded therein. The solid body may be formed of epoxy, polymers and other materials that may enclose a plurality of discrete bodies (e.g., the quantum dots 621) and hold the discrete bodies in a fixed arrangement. The quantum dots 621 are distributed substantially evenly throughout the optical target 620, such that, when irradiated by an excitation light, the quantum dots 621 emit fluorescence in one or more predetermined emission bands of interest. The inspection apparatus 600 may be utilized in the same manner as any other inspection apparatus described herein.

Optionally, the quantum dots 621 may be formed as silicon (Si) quantum dots, such as to enable the wavelength to be tuned.

Figure 6B:
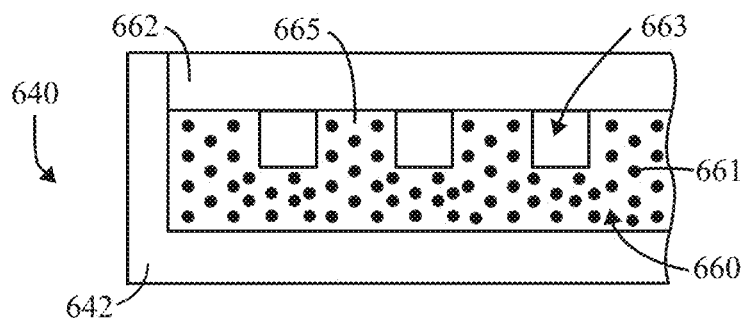
FIG. 6B illustrates a side view of a portion of an inspection apparatus formed in accordance with an alternative example.

FIG. 6B illustrates a portion of an inspection apparatus 640 formed in accordance with an alternative example. The inspection apparatus 640 includes a grating layer 662 and a body 642. An optical target 660 is held within the body 642 and directly engages the grating layer 662. The grating layer 662 includes microstructures 663 formed on a back or bottom surface thereof (relative to an objective). The optical target 660 surrounds and hermetically seals with the microstructures 663. The optical target 660 includes quantum dots 661 distributed throughout. The quantum dots 661 are also provided within regions 665 between the microstructures 663. By way of example, the optical target 660 may be formed from epoxy, a polymer or other composition that will flow into and fill the gap(s) 665 between the microstructures 663 and that will hermetically enclose therein a distributed group of the quantum dots 661.

Figure 6C:
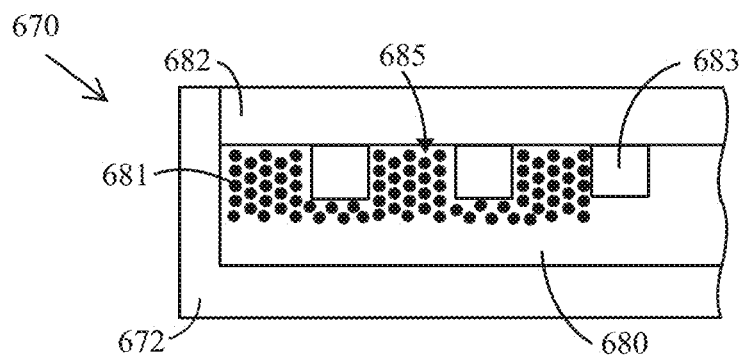
FIG. 6C illustrates a side view of a portion of an inspection apparatus formed in accordance with an alternative example.

FIG. 6C illustrates a portion of an inspection apparatus 670 formed in accordance with an alternative example. The inspection apparatus 670 includes a grating layer 682 and a body 672 and an optical target 680 that is held within the body 672. The optical target 680 directly engages the grating layer 682 and fills gaps 685 between the microstructures 683 formed on the back/bottom side of the grating layer 682. In the example of FIG. 6C, quantum dots 681 are held within the gaps 685 and clustered to be located proximate to and surrounding the microstructures 683. A portion of the optical target 680 that is remote from the microstructures 683 is substantially void of quantum dots 681.

In the examples of FIGS. 6A-6C, the quantum dots 621, 661, 681 may be constructed to emit fluorescence centered about one or more wavelengths of interest depending upon the emission band or emission bands of interest. For example, a portion of the quantum dots 621, 661, 681 may be constructed to emit fluorescence at a wavelength of about 532 nm, while another portion of the quantum dots 621, 661, 681 may be constructed to emit fluorescence at a wavelength of about 660 nm. Optionally, the quantum dots 621, 661, 681 may be constructed to emit at other wavelengths instead of or in addition to the foregoing examples.

Optionally, the fluorescent material may be provided as an organo-polymer. Optionally, the fluorescent material may represent a fluorescent dye embedded within epoxy. As another example, a fluorescent film may be coated on top of an optical target in addition to or in place of doping fluorescent material within a solid host material.

Applications

Examples herein may be used in connection with instruments used for biological or chemical research, including the execution of a large number of controlled reactions. The reactions may be carried out in accordance with a predetermined protocol by automated systems that have, for example, suitable fluidics, optics, and electronics. The systems may be used, for example, to generate a biological or chemical product for subsequent use or to analyze a sample to detect certain properties/characteristics of the sample. When analyzing a sample in some cases, a chemical moiety that includes an identifiable label (e.g., fluorescent label) may be delivered to a chamber where the sample is located and selectively bind to another chemical moiety of the sample. These chemical reactions may be observed or confirmed by exciting the labels with radiation and detecting light emissions from the labels. Such light emissions may also be provided through other means, such as chemiluminescence.

Some known systems use a fluidic device, such as a flow cell, that includes a flow channel (e.g., interior chamber) defined by one or more interior surfaces of the flow cell. The reactions may be carried out along the interior surfaces. The flow cell is typically positioned proximate to an optical assembly that includes a device for imaging the sample within the flow channel. The optical assembly may include an objective lens and/or a solid body imaging device (e.g., charge-coupled device (CCD) or complementary metal-oxide-semiconductor (CMOS)). In some cases, an objective lens is not used and the solid body imaging device is positioned immediately adjacent to the flow cell for imaging the flow channel.

Any example of the inspection apparatus described herein may be used with various systems, methods, assemblies, and apparatuses that detect desired reactions in a sample for biological or chemical analysis. For example, in one sequencing-by-synthesis (SBS) technique, one or more surfaces of the flow channel have arrays of nucleic acid clusters (e.g., clonal amplicons) that are formed through bridge PCR. After generating the clusters, the nucleic acids are "linearized" to provide single stranded DNA (sstDNA). To complete a cycle of sequencing, a number of reaction components are flowed into the flow channel according to a predetermined schedule. For example, each sequencing cycle includes flowing one or more nucleotides (e.g., A, T, G, C) into the flow channel for extending the sstDNA by a single base. A reversible terminator attached to the nucleotides may ensure that only a single nucleotide is incorporated by the sstDNA per cycle. Each nucleotide has a unique fluorescent label that emits a color when excited (e.g., red, green, blue, and the like) that is used to detect the corresponding nucleotide. With the newly-incorporated nucleotides, an image of numerous clusters is taken in four channels (i.e., one for each fluorescent label). After imaging, another reaction component is flowed into the flow channel to chemically cleave the fluorescent label and the reversible terminator from the sstDNA. The sstDNA is then ready for another cycle. Accordingly, a number of different reaction components are provided to the flow channel for each cycle. A single sequencing session may include numerous cycles, such as 100, 300, or more. The inspection apparatus may be constructed to emit fluorescence at the colors utilized by the fluorescent labels in the analysis. The inspection apparatus may be utilized at various points before and/or during the sequencing session.

In some examples, the desired reactions provide optical signals that are detected by an optical assembly. The inspection apparatus may be used to verify, validate, calibrate, etc.

the optical assembly. The optical signals may be light emissions from labels or may be transmission light that has been reflected or refracted by the sample. For example, the optical assembly may be used to perform or facilitate performing a sequencing protocol in which sstDNA is sequenced in a flow cell.

In accordance with examples herein, the inspection apparatus may be used with an optical scanning device and a fluidic cartridge that can be used to provide a sample and reagents to the device. The fluidic cartridge may include a housing that protects various fluidic components such as reservoirs, fluidic connections, pumps, valves and the like. A flow cell may be integrated into the fluidic cartridge in a position where it is in fluid communication with reagents within the housing. For example, the housing may have an opening through which a face of the flow cell is exposed such that it can interact optically with the optical scanning device when the fluidic cartridge is placed in the cartridge receptacle. The device includes one or more microfluorometers.

Figure 7:
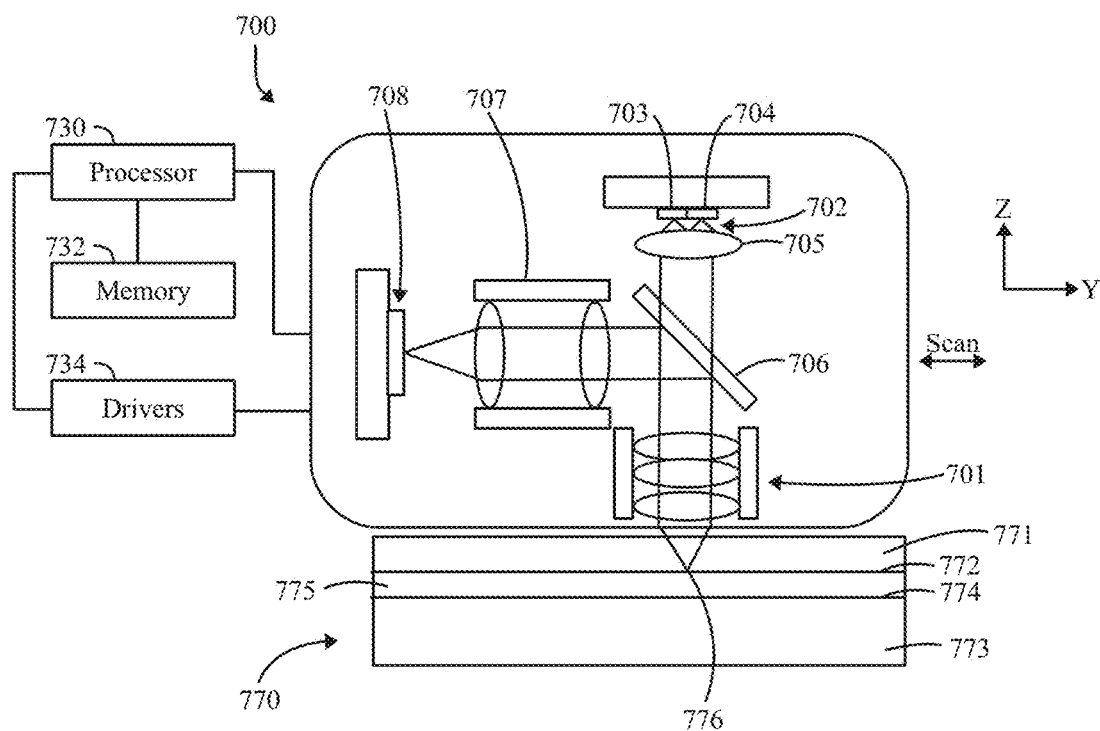
FIG. 7 illustrates a block diagram of an optical detection device formed in accordance with an example.

FIG. 7 illustrates a block diagram of an optical detection device 700 (also referred to as a detector) formed in accordance with an example. The detector 700 includes one or more processors 730 that execute program instructions stored in memory 732 to perform the operations described herein. The processor 730 directs one or more drivers 734 to move the objective 701 in the Z direction and to move the detector 700 in the XY direction. The detector 700 is positioned proximate to a flow cell 770 having an upper layer 771 and a lower layer 773 that are separated by a fluid filled channel 775. In the configuration shown, the upper layer 771 is optically transparent and the detector 700 is focused to an area 776 on the inner surface 772 of the upper layer 771. In an alternative configuration, the detector 700 can be focused on the inner surface 774 of the lower layer 773. One or both of the surfaces 772, 774 can include array features that are to be detected by the detector 700.

The detector 700 includes an objective 701 that is configured to direct excitation radiation from a radiation source 702 to the flow cell 770 and to direct emission from the flow cell 770 to a detector 708. In the example layout, excitation radiation from the radiation source 702 passes through a lens 705 then though a beam splitter 706 and then through the objective on its way to the flow cell 770. In the example shown, the radiation source 702 includes two light emitting diodes (LEDs) 703 and 704, which produce radiation at different wavelengths from each other. The emission radiation from the flow cell 770 is captured by the objective 701 and is reflected by the beam splitter 706 through conditioning optics 707 and to the detector 708 (e.g., a CMOS sensor). The beam splitter 706 functions to direct the emission radiation in a direction that is orthogonal to the path of the excitation radiation. The position of the objective 701 can be moved in the Z direction to alter focus of the microfluorometer. The detector 700 can be moved back and forth in the Y direction to capture images of several areas of the inner surface 772 of the upper layer 771 of the flow cell 770.

The inspection apparatus of FIGS. 1A-1C, 2A-2F, and 6A-6C may be located at a predefined position within the flow cell 770. Optionally, the inspection apparatus may be positioned at a predefined position adjacent to the flow cell 770 within a range of the objective 701. The objective 701 may be moved to the inspection apparatus before, during and/or after a sequencing session, in connection with various types of tests.

Figure 8:
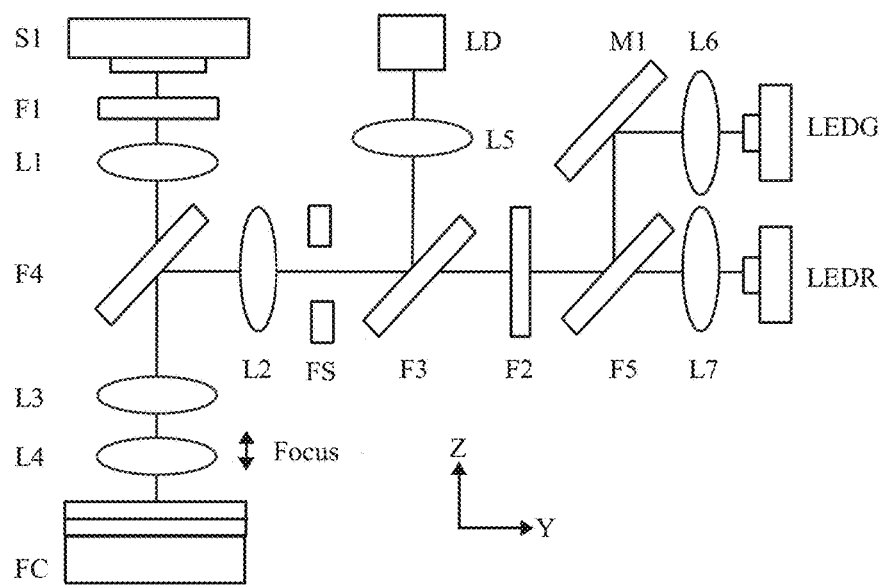
FIG. 8 shows an exploded view of an example microfluorometer for purposes of demonstrating functional arrangement for various optical components in accordance with examples herein.

FIG. 8 shows an exploded view of an example microfluorometer for purposes of demonstrating the functional arrangement for various optical components. Two excitation sources are shown, including a green LED (LEDG) and a red LED (LEDR). Excitation light/radiation from each passes through a green LED collector lens (L6) and red LED collector lens (L7), respectively. An LED fold mirror (M1) reflects the green excitation radiation to a combiner dichroic (F5) which reflects the green excitation radiation through an excitation filter (F2), then through a laser diode beam splitter (F3), then through an excitation field stop (FS), then through an excitation projection lens group (L2) to an excitation/emission dichroic (F4) which reflects the green excitation radiation through a stationary objective lens group (L3) and a translating objective lens group (L4) to the surface of a flow cell (FC). The red excitation radiation passes from the red LED collector lens (L7) to the combiner dichroic (F5) after which the red excitation radiation follows the same path as the green excitation radiation to the surface of the flow cell (FC). As shown in FIG. 8, focusing is actuated by moving the translating objective lens group (L4) up and down (i.e., along the Z direction). Emission from the flow cell (FC) surface passes back through the translating objective lens group (L4), and then through the stationary objective lens group (L3) to the excitation/emission dichroic (F4) which passes the emission radiation to the emission projection les group (L1) through to the emission filter (F1) and then to the CMOS image sensor (S1). A laser diode (LD) is also directed via a laser diode coupling lens group (L5) to the laser diode beam splitter (F3) which reflects the laser diode radiation through the excitation field stop (FS), the excitation projection lens group (L2), the excitation/emission dichroic (F4), the stationary objective lens group (L3) and the translating objective lens group (L4) to the flow cell (FC).

The inspection apparatus of FIGS. 1A-1C, 2A-2F, and 6A-6C may be located at a predefined position within the flow cell (FC). Optionally, the inspection apparatus may be positioned at a predefined position adjacent to the flow cell (FC) within a range of the microfluorometer. The microfluorometer may be moved to the inspection apparatus before, during and/or after a sequencing session, in connection with various types of tests.

Figure 9:
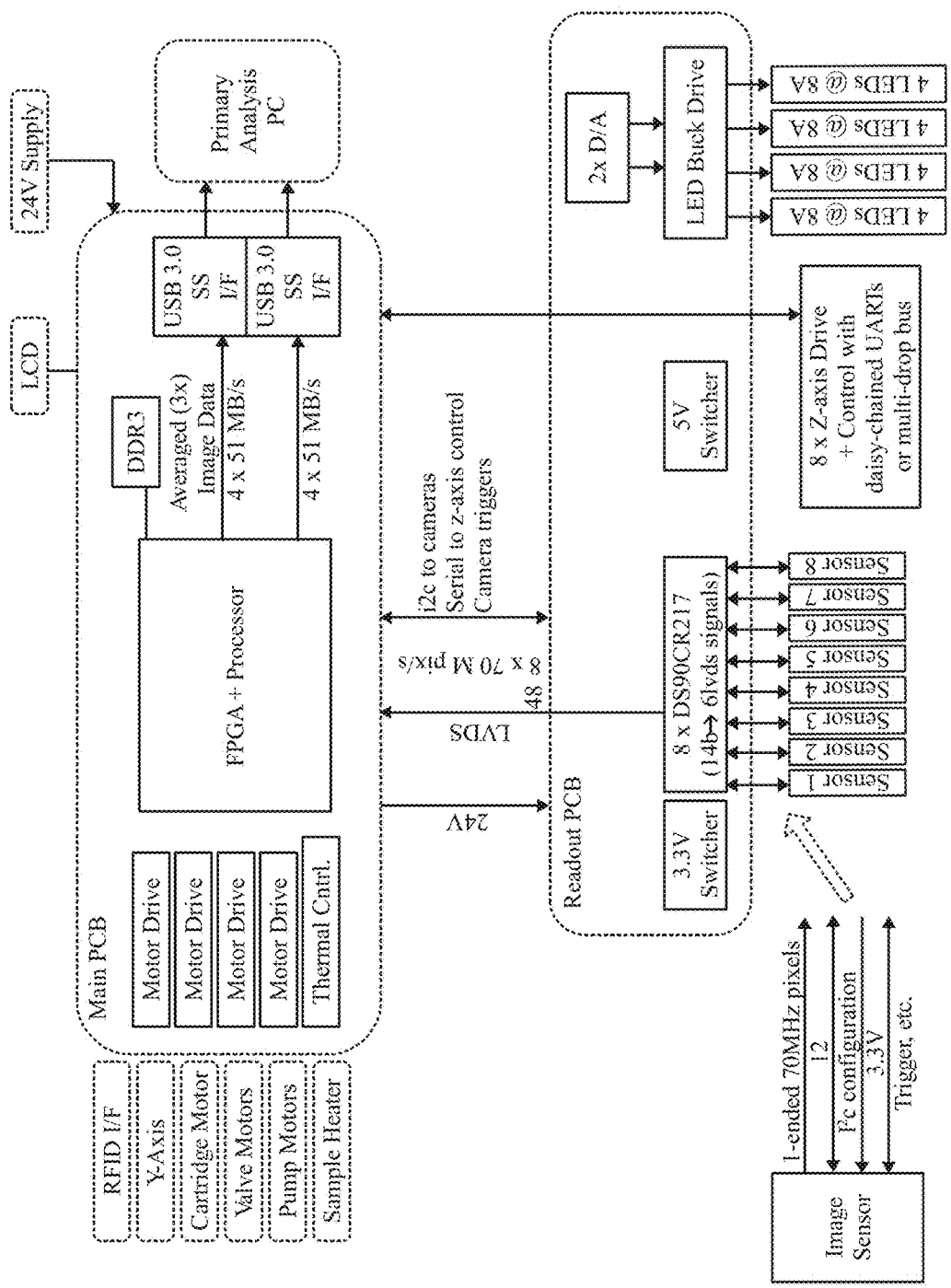
FIG. 9 illustrates a block diagram for a detection apparatus that may utilize an inspection apparatus in accordance with examples herein.

FIG. 9 illustrates a block diagram for a detection apparatus that may utilize an inspection apparatus in accordance with examples disclosed herein. A readout printed circuit board (PCB) is present in a read head and is connected to a main PCB that is typically contained within the detection apparatus housing. In alternative examples, the main PCB can be located exterior to the instrument. Data can be communicated between the readout PCB and main PCB via the LVDS line. The LVDS line can be configured to communicate image data from the readout PCB to the main PCB, and instructions for camera control from the main PCB to the readout PCB.

In the example of FIG. 9, the main PCB is also connected to an exterior primary analysis personal computer (PC) via USB 3.0 SS I/F connectors or other suitable connectors. In some examples the primary analysis computer can be located within the housing of the detection apparatus. However, placing the primary analysis computer off-instrument allows for interchangeable use of a variety of computers to be used for different applications, convenient maintenance of the primary analysis computer by replacement without having to interrupt the activity of the detection apparatus and small footprint for the detection apparatus. Any of a variety of computers, can be used including, for example, a desktop computer, laptop computer, or server containing a processor in operational communication with accessible memory and instructions for implementation of the computer implemented methods described herein. The main PCB is also connected to a liquid crystal display (LCD) for communication to a human user. Other user interfaces can be used as well.

In some examples, a user interface may include a display (e.g., an LCD) to display or request information from a user and a user input device (e.g., a keyboard) to receive user inputs. In some examples, the display and the user input device are the same device. For example, the user interface may include a touch-sensitive display configured to detect the presence of an individual's touch and also identify a location of the touch on the display. However, other user input devices may be used, such as a mouse, touchpad, keyboard, keypad, handheld scanner, voice-recognition system, motion-recognition system, and the like.

The readout PCB includes transmitters for transferring data from individual sensors (i.e., detectors) to the LVDS line, 3.3 volt switching regulator, a 5 volt switching regulator, and LED buck drives for the LED excitation radiation sources. The main PCB includes an FPGA processor configured to accept image data from the LVDS. A DDR3 DIMM frame buffer is electronically connected to the FPGA processor. The main PCB also includes a thermal control regulator and control circuitry for various drive motors such as a Y-axis motor, cartridge motor, valve motor, and pump motor.

The inspection apparatus of FIGS. 1A-1C, 2A-2F, and 6A-6C may be located at a predefined position relative to the detection apparatus of FIG. 9. The detection apparatus may be moved to the inspection apparatus before, during and/or after a sequencing session, in connection with various types of tests.

Any of a variety of characteristics of an image module can be evaluated using the inspection apparatus described herein. Several examples are set forth below in the context of testing a sequencer instrument with an inspection apparatus. It will be understood that similar tests can be carried out for other analytical systems using a different inspection apparatus. Furthermore, details of each test need not be necessary in all applications as will be evident to those skilled in the art when applying the principles exemplified below to alternative analytical systems and inspection apparatus.

Figure 10:
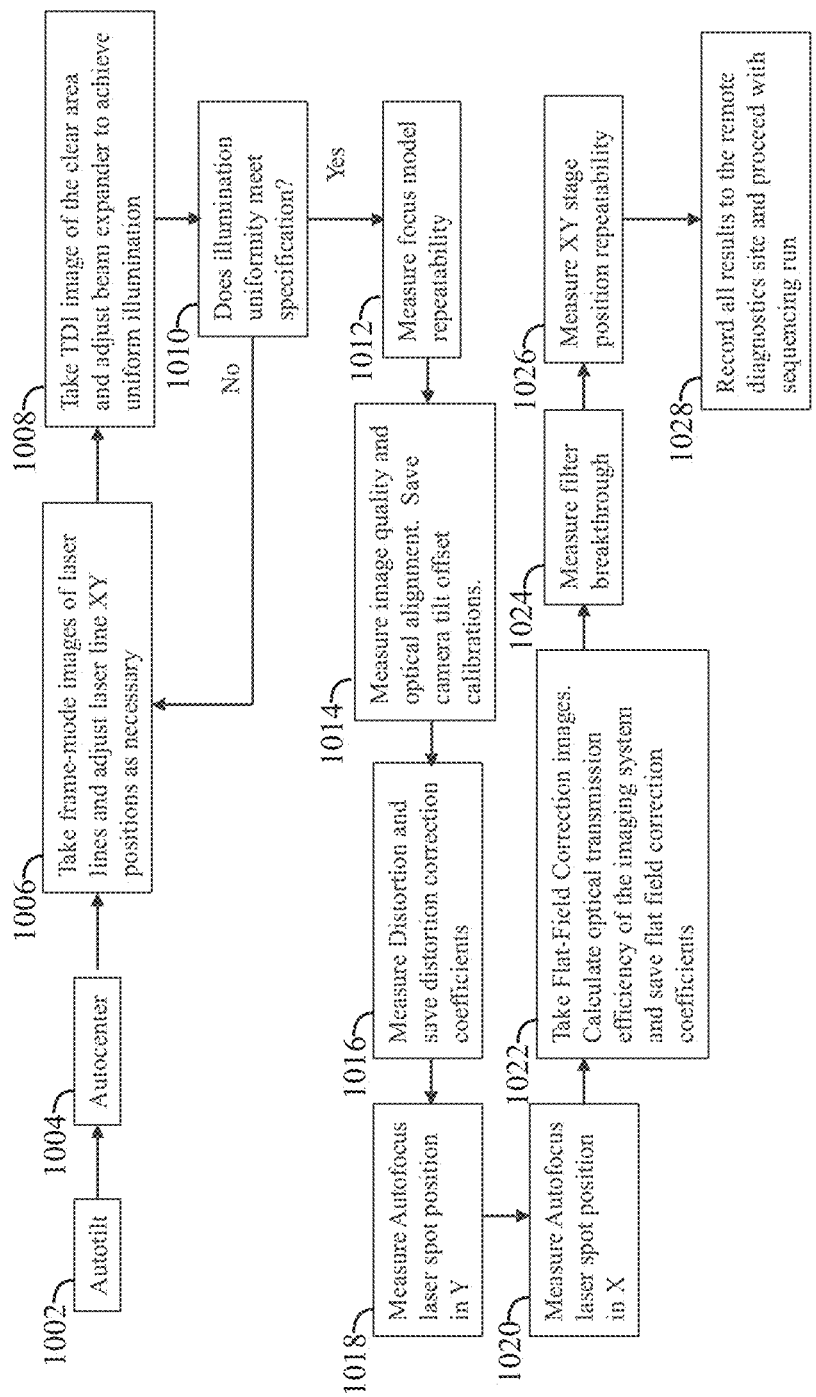
FIG. 10 illustrates an example automated process flow that may be run utilizing an inspection apparatus in accordance with examples herein.

FIG. 10 illustrates an example of various measurements and tests that may be performed utilizing an inspection apparatus formed in accordance with the examples disclosed herein. In accordance with the examples herein, the method of FIG. 10 aligns an objective of an instrument with an optical target that includes a solid body that encloses a fluorescing material. The method of FIG. 10 directs excitation light onto the optical target, detects fluorescence emission from the optical target as reference information and utilizes the reference information in connection with at least one of optical alignment or calibration of the instrument. Various types of reference information are discussed herein. Non-limiting examples of reference information include the information recorded at each of the operations in FIG. 10 (as discussed hereafter).

While the operations of FIG. 10 are described in an order, it is understood that the operations may be performed in alternative orders. Also, it is understood that one or more of the operations of FIG. 10 may be omitted entirely. At 1002, one or more processors of the instrument direct motors to adjust the tilt of the flow cell deck that holds the optical target and sequencing flow cells to perform an auto tilt operation. During the auto tilt operation, the instrument determines and records the final tilt motor coordinates. At 1004, the one or more processors of the instrument direct motors to adjust the XY position of the flow cell deck to perform an auto centering operation. During the auto centering operation, the instrument records the XY stage position of fiducial(s) on the inspection apparatus. The positions of the fiducials are used to monitor drift in the XY stage of the instrument and/or the flow cell deck position when a flow cell is inserted into the instrument.

At 1006, the instrument obtains one or more frame-mode images of the laser lines and adjusts the laser line XY positions accordingly. In connection therewith, the objective is moved to a clear area upon the inspection instrument and adjusted to focus a predetermined depth into the optical target (e.g., 100 µm below the surface of the optical target). Frame-mode images are captured that include laser lines. The XY position of the laser lines is adjusted and additional frame-mode images are captured. The process is repeated until achieving a desired XY position for the laser lines.

At 1008, the instrument collects a time delay and integration (TDI) image of a clear area on the inspection apparatus and adjusts a beam expander of the instrument to achieve uniform illumination. For example, the TDI image may be obtained at a clear tile upon the inspection apparatus with the objective focused a predetermined depth into the optical target. The laser zoom beam expander may be adjusted until a select illumination uniformity is obtained. At 1010, one or more processors of the instrument determine whether the illumination uniformity and laser line position meet predetermined thresholds or specifications. When the illumination uniformity and laser line position do not meet the threshold/specification, flow returns to 1006 where the operations at 1006 and 1008 are repeated. Alternatively, when the illumination uniformity and laser line position meets the thresholds/specifications, flow continues to 1012. Following the operations at 1006 and 1008, the instrument records the final positions of the laser XY pointing actuators and zoom beam expander actuators. The instrument also records the final illumination uniformity, the laser line positions in the X and Y directions, the laser line width and the camera rotation relative to the laser lines.

At 1012, the one or more processors of the instrument measure focus model repeatability. In connection therewith, the objective is moved to an image quality tile on the inspection apparatus, and the instrument obtains focus models and tests the autofocus position repeatability. At 1012, the instrument records the autofocus spot position at the best focus Z position, autofocus laser intensities, autofocus capture range, autofocus gain, autofocus stray light and autofocus Z position repeatability.

At 1014, one or more processors of the instrument measure image quality and optical alignment and save camera tilt offset calibrations. When an instrument auto tilts a sequencing flow cell, the system adjusts certain tilt motors to set the flow cells imaging surfaces parallel to the direction of travel of the X stage. The direction of travel for the XY stage is intended to be perpendicular to the optical axis of the objective. However, slight variations may occur. During manufacturing, the objective and camera may be tilted so that the imaging surface is coplanar to the image of a properly de-tilted flow cell. However, adjustments may occur over time and drift may be introduced. The inspection apparatus may be utilized to measure the camera tilt. To do so, the one or more processors collect a through focus stack of images of a pinhole array and analyze the images to determine the tilt of the chrome layer (microstructures) relative to the camera tilt. The instrument measures the tilt of the chrome layer utilizing one or both of autofocus spots and/or through focus stacks. An error is identified between the camera tilt and the tilt of the chrome layer and corrected by measuring an angle of the chrome layer. By way of example, the angle of the chrome layer may be measured by doing multiple through focus stacks at different X coordinates and comparing the best-focus Z position at each X-coordinate. Additionally or alternatively, the angle of the chrome layer may be measured by detecting the Z position of the chrome layer at multiple X locations using an instrument autofocus system. The camera tilt calibration may be performed at the beginning of each sequencing run, with the tilt motors adjusted to compensate based on the results thereof.

When measuring image quality and optical alignment, the instrument positions the objective over an image quality tile provided on the inspection apparatus. The image quality tile is formed with an array of pinholes through chrome or another microstructure (e.g., 1 µm pinholes on a 3 µm pitch hex pattern). The imaging system within the instrument collects a series of images where the objective is adjusted in the Z position between one or more of the images. As the objective is moved in the Z position between images, the pinholes come into and go out of focus. The series of images with different objective positions are analyzed to identify the image having a desired focus quality (e.g., best focus). For example, the system may determine how tightly the pinholes focus between the series of stacked images, which affords an indication of image quality (e.g., full width at half maximum). As another example, by determining the Z position at which the pinholes come into best focus at various points across the field of view, the system may evaluate axial chromatic shift between different emission colors (e.g., red and green), field curvature, camera tilt and a usable depth of field. At 1014, the instrument records image quality (FWHM), axial chromatism, field curvature and usable depth of field. The instrument also records best focus Z position. The instrument also records camera tilt relative to the X stage and tilt motor offsets to compensate for the camera tilt.

At 1016, one or more processors of the instrument perform a distortion correction calibration by measuring distortion and saving distortion correction coefficients. When imaging pattern flow cells, where each cluster is at a known location, it may be advantageous to compensate for optical distortion in the imaging system in order that the instrument will know where the clusters should appear within the image. The inspection apparatus may be utilized to calibrate for distortion correction at the start of a sequencing run. To do so, the objective is positioned over the distortion correction tile. The distortion correction tile includes pinholes positioned with a predetermined position tolerance across the entire field of view (e.g., 10 nm), thereby providing a pinhole array with a consistent predetermined pinhole spacing. The image is analyzed to identify shifts between the positions of adjacent pinholes across the field of view. The shift is then analyzed, such as by fitting a polynomial to the pinhole shift, where the polynomial indicates where clusters should appear in subsequent images obtained during a sequencing process. At 1016, the instrument records coefficients for distortion correction polynomials, optical magnification, rotation of the flow cell deck and rotation of the Y stage.

At 1018, one or more processors of the instrument performs an autofocus laser spot measurement for the position of one or more lasers in the Y direction. In connection with checking the autofocus laser spot position, the objective is positioned at best focus over the horizontal knife edge which exhibit sharp transitions between clear areas and chrome areas. The autofocus laser spot is bright over chrome areas and very dim over clear areas. A TDI scan is taken using the red and/or green cameras. The images are utilized to identify where the camera fields of view for each emission band of interest are positioned relative to the horizontal knife edge. The objective is then initially positioned over the chrome area and then slowly stepped down in the Y direction until the laser spot disappears, which happens when the laser spot is no longer directed onto a portion of the chrome and instead is entirely directed onto the clear area proximate to the horizontal knife edge. The system may then identify an autofocus spot position in the Y direction relative to the red and green camera's field of view. At 1018, the instrument records the autofocus laser spot position in the Y direction relative to fields of view for emission bands of interest (e.g., relative to red and green fields of view).

At 1020, one or more processors of the instrument performs an autofocus laser spot measurement for the position of one or more lasers in the X direction. In connection with checking the autofocus laser spot position, the objective is positioned over the vertical knife edge which exhibit sharp transitions between clear areas and chrome areas. The autofocus laser spot is bright over chrome areas and very dim over clear areas. A TDI scan is taken using the red and/or green cameras. The images are utilized to identify where the camera fields of view for each emission band of interest are positioned relative to the vertical knife edge. The objective is then initially positioned over the chrome area and then slowly stepped down in the X direction until the laser spot disappears, which happens when the laser spot is no longer directed onto a portion of the chrome and instead is entirely directed onto the clear area proximate to the vertical knife edge. The system may then identify an autofocus spot position in the X direction relative to the red and green camera's field of view. At 1020, the instrument records the autofocus laser spot position in the X direction relative to fields of view for emission bands of interest (e.g., relative to red and green fields of view).

At 1022, one or more processors of the instrument may perform a flat-field correction calibration. In connection therewith, the instrument moves the objective to a clear tile and focuses the objective a predetermined distance below the surface of the optical target, when performing the flat-field correction calibration. The flat-field correction calibration includes obtaining flat field correction images. The one or more processors calculates optical transmission efficiency of the imaging system and saves flat-field correction coefficients in connection therewith. Base calling operations during sequencing is based on intensity of clusters within images. Intensity non-uniformities across a field of view can impact base calling. The instrument would uniformly illuminate clusters within a flow cell to minimize errors, however, it is not always practical to achieve perfectly uniform illumination. A gain and offset of the pixels in the camera are calibrated during manufacturing, however the potential exists that the calibration of camera pixels may change over time and/or with temperature. To perform flat-field correction calibration, the objective is positioned over a clear area of the inspection instrument and focused at a predetermined depth into the optical target (e.g., 100 µm). A measurement is obtained to provide a uniformity baseline for image intensity. Thereafter, at the start of one or more sequencing runs, the instrument may compensate for illumination non-uniformity and camera pixels gain and offset changes by performing the flat-field correction calibration.

The flat-field correction calibration includes obtaining images of the clear area of the inspection apparatus focused to a predetermined depth within the optical target with the lasers shutter closed (to produce a dark image) and with the lasers on at multiple laser powers to get images at different counts of intensity (e.g., about 500, about 1000, about 1500, about 2000, about 2500, about 3000, and about 3500 counts of intensity) in the images. By way of example, and image may be about 1.4 mm long so that the impact of dust, fingerprints, etc. can be averaged out by averaging all pixels in the scanning (Y) dimension. For each of the 3200 pixels (in the non-scanning dimension of the camera), the instrument uses the dark reading and the different intensity readings and fits a polynomial to the data to characterize the response of that pixel (combination of how much light it is exposed to combined with the photo response of that pixel of the camera). When taking images of clusters during sequencing, the instrument uses the measured polynomial response of each pixel and adjusts the intensity of that pixel in the cluster image to make the whole image equivalent to what would be obtained with perfectly uniform illumination and perfectly uniform pixel gain and offsets. At 1022, the instrument records the optical transmission efficiency and the flat-field correction polynomial coefficients for all or at least a portion of the pixels in one or both of the X and Y directions.

At 1024, one or more processors of the instrument checks filter breakthrough and background light. In connection therewith, the instrument moves the objective to a solid chrome tile on the inspection apparatus and performs the filter breakthrough test. For example, a filter breakthrough tile may be formed as a solid chrome region which appears as a mirror. The instrument imaging system is designed to filter out all laser light from hitting the camera. Therefore, when the objective is positioned over a filter breakthrough tile, the system would expect to detect no light at the camera. When light is detected at the camera, the source may be from various factors. For example, the optical filters may not properly filter out all of the laser light. Additionally or alternatively, contaminants in the optical path may be excited by the laser excitation light and fluoresce in the emission band of interest (e.g., red or green). When the optical filter is not properly operating or contaminants exist in the optical path, both circumstances may result in a high background level being detected by the camera. Various corrective measures may be taken. At 1024, the instrument records the filter breakthrough information, background light information and the like.

At 1026, the one or more processors measure the XY stage position repeatability. In connection therewith, the instrument moves the objective to the auto centering fiducial and performs an XY stage position repeatability test. The instrument moves the X and Y stage multiple times from each direction to the auto centering fiducial and after each move it takes an image of the auto centering fiducial. Ideally, the auto centering fiducial would show up at exactly the same position in the image after every move. Movements of the fiducial in the image indicate imperfect positioning of the XY stage. The instrument records the position repeatability in the X and Y directions. The instrument also records the hysteresis exhibited in the X and Y directions. At 1028, the one or more processors records all of the results collected in the foregoing process at a remote diagnostics site. Thereafter, the instrument continues with a sequencing operation.

In connection with the foregoing operations, the instrument may be directed to perform remote diagnostics. By collecting and analyzing images of the inspection apparatus periodically (e.g., at the start of every sequencing run), the instrument may monitor the performance of the imaging system over time. Results can be stored on a local hard drive and/or uploaded to a remote server or cloud server. The diagnostic information may be monitored to monitor the health of the instrument's imaging system and to identify trends in the instrument's performance over time. If any aspect of the imaging system is trending towards failure, repairs may be scheduled before the instrument actually fails. This will increase customer up time. Also, when questions arise as to whether an instrument is experiencing problems with the imaging system, the alignment data may be collected to determine if any aspect of the image system has changed. This will quickly eliminate the imaging system as potential root cause of many issues or may point to a specific issue with the imaging system. If the instrument is not uploading information to the cloud, a field service engineer will be able to trend the data over time by reviewing the historical results stored on the local hard drive.

Further, fluorescent intensity is proportional to dopant concentration. By controlling the dopant concentration (e.g., about 1.1%+/−0.01%), the inspection apparatus can control the measured fluorescence to a desired tolerance (e.g., +/−0.6% in red and +/−0.1% in green). Measuring intensity of the inspection apparatus at a certain scan speed and laser power on one instrument will provide measurement information indicative of an intensity to expect on substantially all similar instruments. The fluorescent intensity measurement from the inspection apparatus can be utilized to indicate whether the instrument is behaving properly (e.g., providing proper laser power delivered to the flow cell, proper amount of fluorescent light collected and delivered to the camera, etc.). Given that the emission characteristics of the inspection apparatus will not change over time, any change in measured fluorescent intensity over the life of the instrument will indicate that either the proper laser power is not being delivered to the flow cell or not all the fluorescent light is being delivered to the camera.

It is recognized that the above operations are non-limiting examples of various operations that may be performed utilizing an inspection apparatus. The above discussed operations may be performed entirely independent of one another and at different points in time. A non-limiting example of remote diagnostics and metrics that may be performed automatically utilizing an inspection apparatus include: Optical transmission efficiency, Image quality (Full-Width-Half-Maximum), Camera tilt, Axial chromatism, Field curvature, Usable depth of field, Distortion, Magnification, Laser line XY positions and line widths, Illumination uniformity, Camera rotation relative to laser lines, Flat field correction coefficients Autofocus Z position repeatability, Autofocus spot position at best focus, Autofocus spot position relative to red and green field of view, Autofocus laser intensity, Autofocus capture range, Autofocus gain, Autofocus stray light, Best-focus Z position, Auto-tilt motor coordinates after autotilt, Hysteresis in X and Y, Position repeatability in X and Y, Rotation of the flow cell deck, Y stage direction of travel, XY stage position of BIRD fiducial, Positions of the laser pointing actuators, and Positions of the laser zoom beam expander actuators.

In accordance with examples herein, an inspection method may include a routine for setting excitation source currents for proper image intensity. The routine can include sequential steps of positioning the inspection apparatus in an imaging module such that an open area of the channel (i.e., with no microstructures) is detected, setting the camera exposure to 1 ms and LED currents to 30%, capturing a dark image with 1 ms exposure and no LEDs on, capturing an image in red and green optical channels with 1 ms exposure, calculating mean intensity of the images, and adjusting LED currents to hit a desired intensity of 2500 counts with 1 ms exposure. LED currents are kept at these values for the remainder of the tests. All subsequent tests can use different exposure times based on the geometry of the microstructure pattern. For example, fiducial tiles and uniformity tiles (lacking microstructures) can be detected with a 1 ms exposure, autofocus tiles can be detected with a 4 ms exposure, image quality tiles can be detected with a 150 ms exposure, and filter breakthrough tiles (fully coated with metal on the interior surface of the upper glass) can be detected with a 500 ms exposure.

In accordance with examples herein, an inspection method can include a routine for excitation source calibration. The routine can be carried out as follows. The XY stage of an instrument is moved to an autofocus tile. A through-focus stack is generated in red and a best-focus Z height is calculated (e.g., step size is 6 µm, exposure time is 4 ms and sweep range is 108 µm). Then the XY stage is moved to a neighboring tile to collect laser images. This is done to mitigate the risk of a manufacturing defect in the inspection apparatus where not all the chrome is removed from inside the 500 micron square opening in the autofocus tile. This defect would make the laser spot intensity too bright at the autofocus tile. The process then collects laser through-focus images (using standard settings for focus model generation) and the laser spot intensity is checked. The step size during these measurements is 2 microns with a Z range that is +/−18 microns. Then the laser exposure time is adjusted until the AF spots are 2000+/−200 counts for "brightest spot" (within +/−18 microns of red best focus). If "save calibrations" is selected on the user interface, then the laser exposure time to use for sequencing is stored.

In accordance with examples herein, a method may include a detector calibration test. As one example, the test can be carried out as follows. Images of an inspection apparatus are obtained at 4 different LED intensities: (1) Dark (LEDs off), (2) Middle low intensity, (3) Middle high intensity, and (4) Bright intensity (about 3000 counts). When taking these images, the XY stage is moved between each image. All tiles in select lanes are used to average out any non-uniform fluorescence (due to debris or fingerprints on top of the inspection). Camera corrections need not be applied to any subsequent tests that were selected.

Closing Statements

It will be appreciated that various aspects of the present disclosure may be embodied as a method, system, computer readable medium, and/or computer program product. Aspects of the present disclosure may take the form of hardware examples, software examples (including firmware, resident software, micro-code, etc.), or examples combining software and hardware aspects that may all generally be referred to herein as a "circuit," "module," or "system." Furthermore, the methods of the present disclosure may take the form of a computer program product on a computer-usable storage medium having computer-usable program code embodied in the medium.

Any suitable computer useable medium may be utilized for software aspects of the present disclosure. The computer-usable or computer-readable medium may be, for example but not limited to, an electronic, magnetic, optical, electro-magnetic, infrared, or semiconductor system, apparatus, device, or propagation medium. The computer readable medium may include transitory examples. More specific examples (a non-exhaustive list) of the computer-readable medium would include some or all of the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission medium such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device.

Program code for carrying out operations of the methods and apparatus set forth herein may be written in an object oriented programming language such as Java, Smalltalk, C++ or the like. However, the program code for carrying out operations of the methods and apparatus set forth herein may also be written in conventional procedural programming languages, such as the "C" programming language or similar programming languages. The program code may be executed by a processor, application specific integrated circuit (ASIC), or other component that executes the program code. The program code may be simply referred to as a software application that is stored in memory (such as the computer readable medium discussed above). The program code may cause the processor (or any processor-controlled device) to produce a graphical user interface ("GUI"). The graphical user interface may be visually produced on a display device, yet the graphical user interface may also have audible features. The program code, however, may operate in any processor-controlled device, such as a computer, server, personal digital assistant, phone, television, or any processor-controlled device utilizing the processor and/or a digital signal processor.

The program code may be locally and/or remotely executed. The program code, for example, may be entirely or partially stored in local memory of the processor-controlled device. The program code, however, may also be at least partially remotely stored, accessed, and downloaded to the processor-controlled device. A user's computer, for example, may entirely execute the program code or only partly execute the program code. The program code may be a stand-alone software package that is at least partly on the user's computer and/or partly executed on a remote computer or entirely on a remote computer or server. In the latter scenario, the remote computer may be connected to the user's computer through a communications network.

The methods and apparatus set forth herein may be applied regardless of networking environment. The communications network may be a cable network operating in the radio-frequency domain and/or the Internet Protocol (IP) domain. The communications network, however, may also include a distributed computing network, such as the Internet (sometimes alternatively known as the "World Wide Web"), an intranet, a local-area network (LAN), and/or a wide-area network (WAN). The communications network may include coaxial cables, copper wires, fiber optic lines, and/or hybrid-coaxial lines. The communications network may even include wireless portions utilizing any portion of the electromagnetic spectrum and any signaling standard (such as the IEEE 802 family of standards, GSM/CDMA/TDMA or any cellular standard, and/or the ISM band). The communications network may even include powerline portions, in which signals are communicated via electrical wiring. The methods and apparatus set forth herein may be applied to any wireless/wireline communications network, regardless of physical componentry, physical configuration, or communications standard(s).

Certain aspects of present disclosure are described with reference to various methods and method steps. It will be understood that each method step can be implemented by the program code and/or by machine instructions. The program code and/or the machine instructions may create means for implementing the functions/acts specified in the methods.

The program code may also be stored in a computer-readable memory that can direct the processor, computer, or other programmable data processing apparatus to function in a particular manner, such that the program code stored in the computer-readable memory produce or transform an article of manufacture including instruction means which implement various aspects of the method steps.

The program code may also be loaded onto a computer or other programmable data processing apparatus to cause a series of operational steps to be performed to produce a processor/computer implemented process such that the program code provides steps for implementing various functions/acts specified in the methods of the present disclosure.

The terms "substantially" and "about" used throughout this disclosure, including the claims, are used to describe and account for small fluctuations, such as due to variations in processing. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

The terms "comprise," "include," "contain," etc., and variations thereof, that are used in the specification and claims herein are intended to be open-ended, including not only the recited elements, but further encompassing any additional elements. Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

It is to be understood that the ranges provided herein include the stated range and any value or sub-range within the stated range. For example, a range represented by equals or is between four and ten (4 to 10), should be interpreted to include not only the explicitly recited limits of from 4 to 10, but also to include individual values, such as about 6, 7.5, 9, etc., and sub-ranges, such as from about 5 to about 8, etc.

While several examples have been described in detail, it is to be understood that the disclosed examples may be modified. Therefore, the foregoing description is to be considered non-limiting.

What is claimed is:

1. An inspection apparatus, comprising:
   an optical target including a solid host material and a fluorescing material embedded in the solid host material, the solid host material having a predetermined phonon energy $HOST_{PE}$;
   a body having a pocket to receive the optical target, wherein the body includes an inset region located at a top surface and surrounding the pocket; and
   a transparent layer mounted in the inset region and positioned above the optical target;
   wherein the body includes a channel at least partially surrounding the pocket, the channel to receive an adhesive to bond to a grating layer, wherein the channel includes a series of pressure relief pockets distributed about the channel, the pressure relief pockets to relieve stress induced onto the grating layer by the adhesive during a curing process;
   wherein the fluorescing material exhibits a select ground energy level and a target excitation (TE) energy level separated from the ground energy level by a first energy gap corresponding to a fluorescence emission wavelength of interest (FEWI), the fluorescing material having a next lower lying (NLL) energy level relative to the TE energy level, the NLL energy level spaced a second energy gap $FM_{EG2}$ below the TE energy level wherein a ratio of the $FM_{EG2}/HOST_{PE}$ is three or more.

2. The apparatus of claim 1, wherein the ratio of the $FM_{EG2}/HOST_{PE}$ equals or is between four and ten.

3. The apparatus of claim 1, wherein the solid host material includes at least one of glass, amorphous polymers, crystalline materials, semi-crystalline polymers, metallic glass, or ceramic.

4. The apparatus of claim 1, wherein the fluorescing material represents an ion of at least one of a rare-earth element or a transition metal element.

5. The apparatus of claim 1, wherein the solid host material has a maximum phonon energy less than or equal to 580 cm$^{-1}$.

6. The apparatus of claim 1, wherein the fluorescence emission wavelength of interest has a center wavelength at or below about 1000 nm.

7. The apparatus of claim 1, wherein the body further includes a diffusion well located below the pocket, the diffusion well to receive excitation light passing through the optical target, the diffusion well including a well bottom having a surface finish that exhibits a reflectively of no more than about 20.0%.

8. The apparatus of claim 1, further comprising microstructures formed on a surface of at least one of the transparent layer or the optical target to form a grating layer.

9. The apparatus of claim 1, further comprising an anti-reflective coating formed on a surface of at least one of the transparent layer or the optical target.

* * * * *

UNITED STATES PATENT AND TRADEMARK OFFICE
CERTIFICATE OF CORRECTION

PATENT NO. : 10,261,018 B2
APPLICATION NO. : 15/837901
DATED : April 16, 2019
INVENTOR(S) : John Gerhardt Earney et al.

It is certified that error appears in the above-identified patent and that said Letters Patent is hereby corrected as shown below:

On the Title Page

Column 1 (Inventors), delete "Dajun A. Yuan," and insert -- Dajun Yuan, --, therefor.

In the Claims

In Column 40, Line 56, in Claim 7, delete "reflectively" and insert -- reflectivity --, therefor.

Signed and Sealed this
Seventeenth Day of September, 2019

Andrei Iancu
*Director of the United States Patent and Trademark Office*